(12) United States Patent
Kraus et al.

(10) Patent No.: US 11,737,460 B2
(45) Date of Patent: Aug. 29, 2023

(54) PERFORMIC ACID ON-SITE GENERATOR AND FORMULATOR

(71) Applicant: ECOLAB USA INC., Saint Paul, MN (US)

(72) Inventors: Paul R. Kraus, Saint Paul, MN (US); Benjamin Crew, Saint Paul, MN (US); Junzhong Li, Saint Paul, MN (US); David D. McSherry, Saint Paul, MN (US); Ramakrishnan Balasubramanian, Saint Paul, MN (US); Richard Staub, Saint Paul, MN (US); Ariel Chatman Kleczewski, Saint Paul, MN (US); Minh Tran, Saint Paul, MN (US); Catherine Hanson, Saint Paul, MN (US); Irwan Yunus, Saint Paul, MN (US); Jeffery D. Breshears, Saint Paul, MN (US); Brian Paul Brunner, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 430 days.

(21) Appl. No.: 16/946,513

(22) Filed: Jun. 25, 2020

(65) Prior Publication Data
US 2020/0323205 A1 Oct. 15, 2020

Related U.S. Application Data

(63) Continuation of application No. 16/183,571, filed on Nov. 7, 2018, now Pat. No. 10,729,131, which is a
(Continued)

(51) Int. Cl.
*A01N 37/36* (2006.01)
*A01N 37/16* (2006.01)
(Continued)

(52) U.S. Cl.
CPC ............ *A01N 37/36* (2013.01); *A01N 37/16* (2013.01); *A23L 3/3463* (2013.01);
(Continued)

(58) Field of Classification Search
CPC .... C07C 231/065; B01J 19/245; A01N 37/36; A23L 3/3499; A61L 2/18
(Continued)

(56) References Cited

U.S. PATENT DOCUMENTS

| | | |
|---|---|---|
| 5,037,955 A | 8/1991 | Dighton et al. |
| 5,141,731 A | 8/1992 | Meier et al. |

(Continued)

FOREIGN PATENT DOCUMENTS

| | | |
|---|---|---|
| AU | 2007311532 B2 | 6/2012 |
| CA | 2475361 A1 | 8/2003 |

(Continued)

OTHER PUBLICATIONS

Oties, Semih, "Methods of Analysis of Food Components and Additives", CRC Press 2011, p. 89, published on Oct. 2, 2011.
(Continued)

*Primary Examiner* — Monzer R Chorbaji
(74) *Attorney, Agent, or Firm* — McKee, Voorhees & Sease, PLC

(57) ABSTRACT

Methods of generating performic acid by contacting aqueous oxidizing agent and aqueous formic acid source in liquid phase are disclosed. A system and apparatus for the in situ production of the performic acid chemistries is further disclosed. In particular, a continuous flow reactor is provided to generate performic acid at variable rates. Methods of employing the oxidizing biocide for various disinfection applications are also disclosed.

20 Claims, 14 Drawing Sheets

Related U.S. Application Data continuation of application No. 15/254,559, filed on Sep. 1, 2016, now Pat. No. 10,172,351.

(60) Provisional application No. 62/303,746, filed on Mar. 4, 2016, provisional application No. 62/214,340, filed on Sep. 4, 2015.

(51) Int. Cl.

| | |
|---|---|
| *B01J 19/18* | (2006.01) |
| *A23L 3/3499* | (2006.01) |
| *C07C 407/00* | (2006.01) |
| *A23L 3/3463* | (2006.01) |
| *A23L 3/3481* | (2006.01) |
| *C23F 11/10* | (2006.01) |
| *B01J 19/24* | (2006.01) |
| *C07C 51/367* | (2006.01) |

(52) U.S. Cl.
CPC .......... *A23L 3/3481* (2013.01); *A23L 3/3499* (2013.01); *B01J 19/1812* (2013.01); *B01J 19/1818* (2013.01); *B01J 19/2415* (2013.01); *C07C 51/367* (2013.01); *C07C 407/00* (2013.01); *C23F 11/10* (2013.01); *A23V 2002/00* (2013.01); *B01J 2219/00051* (2013.01); *B01J 2219/00094* (2013.01); *B01J 2219/00132* (2013.01); *B01J 2219/00144* (2013.01); *Y02W 10/37* (2015.05)

(58) Field of Classification Search
USPC .............................. 422/1, 28, 129, 256, 300
See application file for complete search history.

(56) References Cited

U.S. PATENT DOCUMENTS

| | | | |
|---|---|---|---|
| 5,246,620 A | 9/1993 | Gethoffer et al. | |
| 5,250,707 A | 10/1993 | Inaba et al. | |
| 5,266,587 A | 11/1993 | Sankey et al. | |
| 5,391,324 A | 2/1995 | Reinhardt et al. | |
| 5,422,028 A | 6/1995 | Oakes et al. | |
| 5,463,112 A | 10/1995 | Sankey et al. | |
| 5,466,825 A | 11/1995 | Carr et al. | |
| 5,576,282 A | 11/1996 | Miracle et al. | |
| 5,616,281 A | 4/1997 | Hardy et al. | |
| 5,616,335 A | 4/1997 | Nicolle et al. | |
| 5,718,910 A | 2/1998 | Oakes et al. | |
| 5,817,614 A | 10/1998 | Miracle et al. | |
| 5,914,303 A | 6/1999 | Sankey et al. | |
| 5,928,382 A | 7/1999 | Reinhardt et al. | |
| 6,049,001 A | 4/2000 | Mattila et al. | |
| 6,049,002 A | 4/2000 | Mattila et al. | |
| 6,068,815 A | 5/2000 | Oberleitner et al. | |
| 6,156,156 A | 12/2000 | Rousu et al. | |
| 6,211,237 B1 | 4/2001 | Huss et al. | |
| 6,262,013 B1 | 7/2001 | Smith et al. | |
| 6,274,542 B1 | 8/2001 | Carr et al. | |
| 6,284,719 B1 | 9/2001 | Simms | |
| 6,537,958 B1 | 3/2003 | Di Capua et al. | |
| 6,548,467 B2 | 4/2003 | Baker et al. | |
| 6,548,470 B1 | 4/2003 | de Buzzaccarini et al. | |
| 6,693,069 B2 | 2/2004 | Körber et al. | |
| 6,841,090 B1 | 1/2005 | Serego Allighieri et al. | |
| 7,494,963 B2 | 2/2009 | Ahmed et al. | |
| 7,547,421 B2 * | 6/2009 | McSherry | B01J 19/0006 562/2 |
| 7,682,403 B2 | 3/2010 | Gohl et al. | |
| 8,110,603 B2 | 2/2012 | Kawabata et al. | |
| 8,426,634 B2 | 4/2013 | Neas et al. | |
| 8,729,296 B2 | 5/2014 | Fast et al. | |
| 8,802,061 B2 | 8/2014 | Tichy et al. | |
| 8,828,910 B2 | 9/2014 | Aksela et al. | |
| 8,858,895 B2 | 10/2014 | Kraus et al. | |
| 8,877,354 B2 | 11/2014 | Horiuchi et al. | |
| 8,889,900 B2 | 11/2014 | Kraus et al. | |
| 8,933,263 B2 | 1/2015 | Herdt et al. | |
| 8,957,246 B2 | 2/2015 | McSherry et al. | |
| 9,012,504 B2 | 4/2015 | Olson et al. | |
| 9,034,390 B2 | 5/2015 | Kielbania, Jr. | |
| 9,044,403 B2 | 6/2015 | Shultz | |
| 9,192,909 B2 | 11/2015 | Kraus et al. | |
| 9,288,992 B2 | 3/2016 | Li et al. | |
| 9,321,664 B2 | 4/2016 | Li et al. | |
| 9,585,397 B2 | 3/2017 | Li et al. | |
| 9,676,711 B2 | 6/2017 | Junzhong et al. | |
| 9,701,931 B2 | 7/2017 | Moore | |
| 9,752,105 B2 | 9/2017 | Stokes et al. | |
| 2002/0161258 A1 | 10/2002 | Miracle et al. | |
| 2006/0177518 A1 | 8/2006 | Stevenson et al. | |
| 2007/0093407 A1 | 4/2007 | Bianchetti et al. | |
| 2007/0249712 A1 | 10/2007 | Dee et al. | |
| 2010/0297719 A1 | 11/2010 | de Sa et al. | |
| 2011/0233067 A1 | 9/2011 | Lind et al. | |
| 2012/0164236 A1 | 6/2012 | Iwasa et al. | |
| 2013/0203849 A1 | 8/2013 | Ben Yehuda | |
| 2013/0247308 A1 | 9/2013 | Duerrschmidt et al. | |
| 2014/0120179 A1 | 5/2014 | Smith et al. | |
| 2014/0121272 A1 | 5/2014 | Smith et al. | |
| 2014/0311612 A1 | 10/2014 | Hoglund | |
| 2015/0018319 A1 | 1/2015 | Larson et al. | |
| 2017/0020130 A1 | 1/2017 | Buschmann et al. | |
| 2017/0064949 A1 | 3/2017 | Kraus et al. | |
| 2017/0118989 A1 | 5/2017 | Oppong et al. | |
| 2017/0245499 A1 | 8/2017 | Fast et al. | |

FOREIGN PATENT DOCUMENTS

| | | |
|---|---|---|
| EP | 0231632 A2 | 8/1987 |
| EP | 1022946 B1 | 8/2000 |
| EP | 1114137 B1 | 7/2001 |
| EP | 1129171 B1 | 9/2001 |
| EP | 1125497 B1 | 6/2003 |
| EP | 1131016 B1 | 2/2005 |
| EP | 1926808 B1 | 6/2008 |
| EP | 2471941 B1 | 7/2012 |
| EP | 2714877 B1 | 7/2017 |
| EP | 2566943 B1 | 9/2017 |
| FR | 1432773 A | 3/1966 |
| WO | 9420424 A1 | 9/1994 |
| WO | 9504128 A1 | 2/1995 |
| WO | 9533816 A1 | 12/1995 |
| WO | 9804659 A3 | 2/1998 |
| WO | 9955439 A1 | 11/1999 |
| WO | 2000045639 A1 | 8/2000 |
| WO | 2008047263 A3 | 4/2008 |
| WO | 2008088873 A1 | 7/2008 |
| WO | 2011089313 A2 | 7/2011 |
| WO | 2015118357 A2 | 8/2015 |
| WO | 2016100694 A1 | 6/2016 |
| WO | 2016100700 A1 | 6/2016 |
| WO | 2017007416 A1 | 1/2017 |
| WO | 2017044806 A1 | 3/2017 |
| WO | 2017165408 A1 | 9/2017 |

OTHER PUBLICATIONS

"International Search Report and the Written Opinion of the International Searching Authority", International Application No. PCT/US2016/050099, 14 pages, dated Nov. 17, 2016.

Ebrahimi et al., "Heterogeneously Catalyzed Synthesis of Performic Acid in a Microstructured Reactor", Chemical Engineering Journal, 179, pp. 312-317, 2012.

* cited by examiner

PERFORMIC ACID ON-SITE GENERATOR AND FORMULATOR

CROSS-REFERENCE TO RELATED APPLICATIONS

This is a Continuation Application of U.S. Ser. No. 16/183,571, filed Nov. 7, 2018, which is a Continuation Application of U.S. Ser. No. 15/254,559, filed Sep. 1, 2016, now U.S. Pat. No. 10,172,351, issued Jan. 8, 2019, which claims priority to U.S. Provisional Application Ser. No. 62/214,340 filed on Sep. 4, 2015 and U.S. Provisional Application Ser. No. 62/303,746 filed on Mar. 4, 2016, each entitled "Performic Acid On-Site Generator and Formulator," the entire disclosure of which are incorporated herein by reference.

FIELD OF THE INVENTION

The present invention relates to methods of on-site generation of performic acid using a generator or formulated system. The formation of performic acid is achieved on-site by contacting an aqueous oxidizing agent and aqueous formic acid in liquid phase under heated laminar or turbulent flow conditions. In particular, a continuous flow reactor is provided to generate performic acid at variable rates, including near instantaneous generation. The on-site generated performic acid and/or mixed peracid composition is suitable for providing an oxidizing biocide for various disinfection applications. The generated performic acid compositions are useful for treating a target, e.g., surface(s) and/or other items used in papermaking, textiles, food, or pharmaceutical industry, target water and/or treating a biofilm.

BACKGROUND OF THE INVENTION

Performic acid (or peroxyformic acid) is considered an industrially important percarboxylic acid. Performic acid has an advantageous degree and range of microbiocidal properties compared to other peroxycarboxylic acids, such as peracetic and perproprionic acids, as disclosed by V. Merka et al in J. Hyg. Epidem. Microbiol. Immunol, 1965 (IX) 220, as well as in European Patent Application No. 863,098,96.

Peroxycarboxylic acid compositions are generally made through an acid catalyzed equilibrium reaction. Most often, the peroxycarboxylic acids are generated in a chemical plant, and then shipped to customers for on-site use. Due to the limited storage stability of peroxycarboxylic acids, the peroxycarboxylic acids must be packed in special containers and shipped under strict Department of Transportation (DOT) guidelines. Further, excess amounts of reagents (e.g., acids, oxidizing agents, and stabilizers) are present in the compositions during shipping to prevent decomposition. For peroxyformic acid, however, the inherent instability of the substance relative to the higher alkyl peracid, and the explosive nature of the substance at the concentrate make it an even more significant challenge to be manufactured, stored and transported before dilution prior to use, in the similar way like higher alkyl peracid. Thus, there are needs for the on-site generation of peroxycarboxylic acids, especially peroxyformic acid.

Performic acid is formed by part of the original reagents and reaction products form an equilibrium mixture. However, such a mixture may be rather unstable and/or reactive in handling and in storage, typically having a relative short shelf life. The stability of performic acid, in comparison to other peroxycarboxylic acids such as peracetic acid, presents stability challenges from 1-2 orders greater. For example, the half-life of performic acid is in the order of minutes to hours, compared to the half-life of peracetic acid which is weeks to months. Due to the characteristics of performic acid in having significantly lower shelf life stability there remains a need to provide in situ generation for use on-site without requiring storage and/or shipment.

Performic acid is extremely useful and effective in various field of technology such as disinfection, in spite of its instability. Formed from the reaction of hydrogen peroxide and formic acid, it reacts more rapidly and powerfully than peracetic acid before breaking down to water and carbon dioxide. Performic acid is an environmentally friendly oxidizing biocide for various disinfection applications. The application areas involve microbial growth control and cleaning of surfaces in larger industrial scale such as municipal or industrial waste water purification, or for circulation of process waters in pulp and paper industry. These compositions are most applicable for example in hospitals, dental surgeries, kitchens, and bathrooms to kill infectious organisms.

Performic acid solutions are highly reactive. If performic acid solutions are contacted with impurities such as zinc dust, lead dioxide, or sodium azide they may react violently and decompose. Performic acid typically decomposes as such into carbon dioxide and water within a few hours at ambient temperature and pressure.

Typically, performic acid is formed by reacting aqueous formic acid with aqueous hydrogen peroxide through an exothermic reaction in the present of a strong mineral acid catalyst, such as sulfuric acid. Due to its instability, performic acid solutions should be prepared in situ preferably at the point of use or directly before use depending on the properties of the reactants and reaction points. However, the presence of strong mineral acid, such as sulfuric acid, in pipes can lead to corrosion of the material and contamination of the process stream.

Accordingly, it is an objective of the invention to provide a method for generating performic acid in situ without the presence of an acid catalyst, such as a strong mineral acid catalyst.

A further objective of the invention includes providing a method for generating performic acid in situ employing with heat as the only catalyst, without additional chelating and/or stabilizing agents.

A still further objective of the invention is to provide on-site generator apparatus for a continuous flow reaction with variable rates of generating performic acid.

Additional objectives of the invention include generating the performic acid as well as mixed peracid compositions including performic acid in situ. Other objects, advantages and features of the present invention will become apparent from the following specification taken in conjunction with the accompanying drawings.

BRIEF SUMMARY OF THE INVENTION

In an embodiment, the present invention provides an adjustable biocide formulator or generator system for on-site performic acid forming composition generation. The formulator or generator system comprises at least one inlet, a length of pipe, a heating device, and an outlet for dosing a performic acid forming composition. In an aspect, the inlet(s) are in fluid connection with the length of pipe and supply reagents to produce performic acid in the length of pipe. In a further aspect, the reagents comprise a formic acid source and an oxidizing agent. In a further aspect, the length of pipe is in fluid connection with the outlet to dispense the performic acid forming composition.

In an embodiment, the present invention provides a method of on-site generating performic acid forming composition comprising: providing a formic acid source to a length of pipe at a desired flow rate; providing an oxidizing agent to said length of pipe at a desired flow rate; contacting said formic acid source with an effective amount of said oxidizing agent within said length of pipe in the presence of a heating device to form a performic acid; delivering said performic acid to a downstream process. In a further aspect, the method includes a heating device that provides sufficient heat to raise the temperature of the solution within the length of a pipe to a temperature not exceeding 180° C. and wherein said heating device is a cartridge (for example) contained with said length of pipe and wherein the difference between said pipe's inner diameter and said cartridge's diameter is less than about 5 inches. In a further aspect, the method includes cooling said performic acid to a temperature at or below freezing. In a still further aspect, the method includes measuring variables including conductivity, temperature, product levels, concentrations, IR/UV/VIS spectroscopy, pressure, performic acid and/or oxidant concentrations, and/or flow rate and controlling the method using control software for operating said apparatus to generate a user- or system-inputted performic acid forming composition and said desired flow rate of said performic acid forming composition for on-site generation. In a further aspect, the present invention includes a performic acid compositions formed using the method of the invention.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

Figure 1:
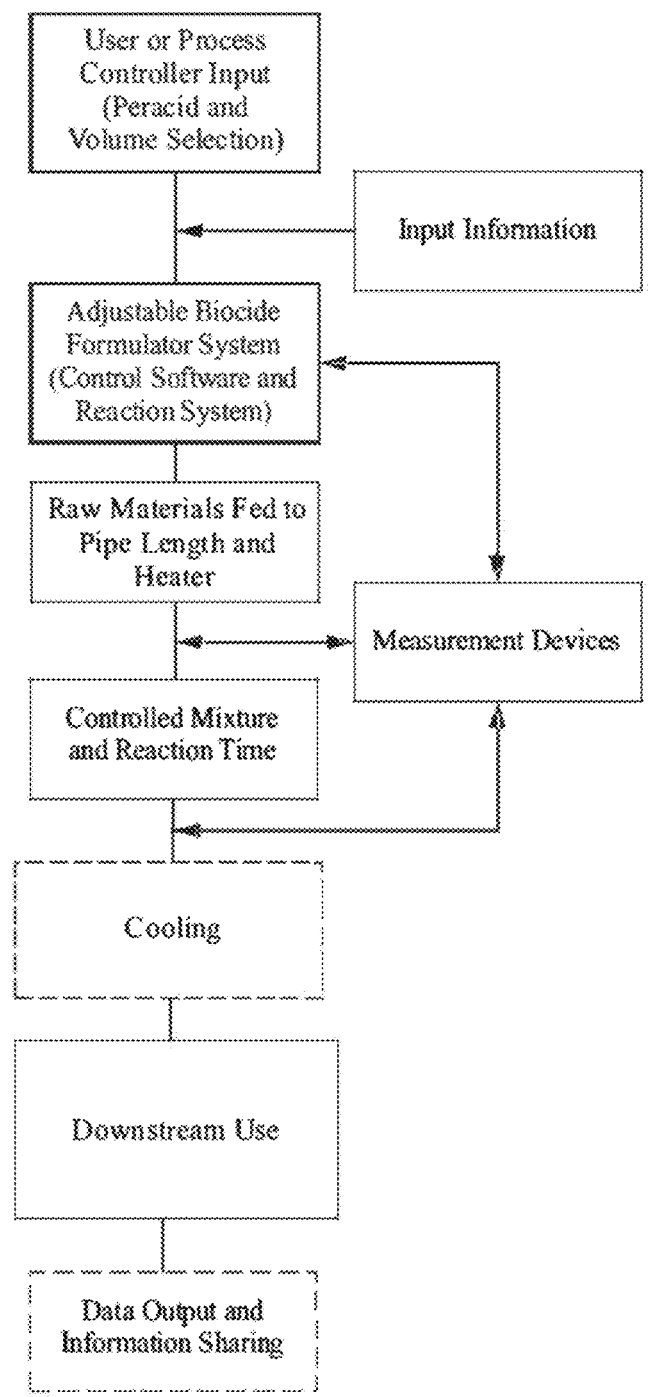
FIG. 1 shows a schematic diagram of a user or controller operated adjustable biocide formulator apparatus according to an embodiment of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to performic acid formulator or generator systems for on-site performic acid generation, including mixed peracid compositions comprising performic acid, as well as methods of making and using such compositions. The compositions and systems for making the compositions disclosed herein have many advantages over conventional systems and methods for making performic acid compositions. For example, the system allow on-site, user- or system-controlled formulation, eliminating the step of storing unstable performic acid compositions. In addition, there are various advantages of the compositions, including having significantly lower reactant inputs, increased stability, and ability to be generated in situ or on-site.

The embodiments of this invention are not limited to particular methods and systems for on-site generation of performic acid, which vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein. In describing and claiming the embodiments of the present invention, the headings provided are not limitations on the embodiments of the invention and the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g., red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "fouling" shall be understood to mean the undesirable presence of or any deposition of any organic or inorganic material in the applicable composition or chemistry.

As used herein, the term "free" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any non-cellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "performic acids" or "performic acid composition" refer to a composition or mixture including performic acid and at least one other peroxycarboxylic acid.

As used herein, the terms "performic acid" or "peroxyformic acid" refer to an acid having the formula of $CH_2O_3$ and the structure:

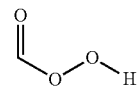

In general, performic acid is generated by combining formic acid and hydrogen peroxide under acidic conditions to yield performic acid and water (as shown) and one skilled in the art will ascertain that additional carboxylic acids and percarboxylic acids could further be included in the generation steps according to the present invention.

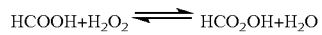

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25+/−2° C., against several test organisms.

For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrylonitrile-butadiene-styrene polymers (ABS), and polysulfone polymers (PS). Another exemplary plastic that can be cleaned using the compounds and compositions of the invention include polyethylene terephthalate (PET).

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Embodiments of the Invention—Performic Acid Chemistries

According to an embodiment of the invention methods and apparatus for on-site generation of performic acid chemistries for use as cleaning agents including for example, antimicrobial applications, bleaching applications, and other cleaning and anti-scaling applications. The methods and apparatus according to the invention are capable of on-site generation of performic acid chemistries according to user-specifications. As referred to herein, performic acid chemistries are further understood to include mixed performic acid chemistries. The invention overcomes the shortfalls of commercial-available performic acid by providing user-specific formulations with enhanced performance efficacy. In addition, the methods and apparatus use heat as the reaction catalyst, beneficially reducing the costs and hazards associated with transporting active chemistries, providing active chemistries with increased shelf-lives and reduction of waste of active chemistries as a result of on-site user-identified performic acid production according to the invention.

The methods and apparatus of the present invention overcome significant limitations of conventional methods of performic acid generation, typically acid catalyzed equilibrium reactions. The methods and apparatus of the present invention overcome the many downsides to such conventional methods, including, but not limited to elimination of the use of excess amounts of reactants, and hazardous shipping conditions.

While an understanding of the mechanism is not necessary to practice the present invention and while the present invention is not limited to any particular mechanism of action, it is contemplated that, in some embodiments the benefits afforded according to the invention result from the use of heat as the sole catalyst in the methods and apparatus of the present invention for generating on-site performic acid. Beneficially, the reacted performic acids according to the invention are obtained in greater amounts than in equilibrium chemistry wherein greater amounts of oxidizing agent, e.g. hydrogen peroxide, and other reagents would be present. According to the present invention, an aqueous solution of the performic acid(s) produced contains a relatively higher concentration of performic acid(s) compared to unreacted oxidizing agent, e.g. hydrogen peroxide component. Preferably, the average performic acid concentration is at least 1 wt-%, at least 2 wt-%, at least 3 wt-%, at least 4 wt-%, at least 5 wt-%, at least 6 wt-%, at least 7 wt-%, at least 8 wt-%, at least 9 wt-%, at least 10 wt-%, at least 11 wt-%, at least 12 wt-%, at least 13 wt-%, at least 14 wt-%, or at least 15 wt-%. More preferably, the average performic acid concentration is at least 2 wt-%, and more preferably the average performic acid concentration is at least 5.5 wt-%. This is significantly advantageous for the antimicrobial and other cleaning applications disclosed herein as desirable according to the embodiments of the invention. However, as one skilled in the art will appreciate, the average performic acid concentration will vary depending on heating, flow rate, temperatures, pressures, concentration of the reagents, etc.

Rather than providing a performic acid composition in an equilibrium mixture, in situ generation of the performic acid composition allows the performic acid to be produced stoichiometrically through selecting the composition of the starting materials. The in situ systems of the present invention therefore generate higher concentrations of the performic acids than are available in equilibrium systems. In particular, according to the invention the systems generate higher concentrations of the performic acid and lower concentrations of hydrogen peroxide (e.g. unreacted reagents) than achieved in equilibrium systems. Preferably, the average performic acid concentration is at least 1 wt-%. More preferably, the average performic acid concentration is at least 5 wt-%, and more preferably the average performic acid concentration is at least 5.5 wt-%. Preferably, the average hydrogen peroxide concentration is less than 10 wt-%. More preferably, the average hydrogen peroxide concentration is less than 5 wt-% and more preferably, the average hydrogen peroxide concentration is less than 1 wt-%. However, as one skilled in the art will appreciate, the average concentration of performic acid and/or hydrogen peroxide will vary depending on heating, flow rate, temperatures, pressures, concentration of the reagents, etc.

In some aspects, the methods of the present invention generate performic acid(s) without the need for additional chelating and/or stabilizing agents, although such agents are compatible with these systems they are not required components. Instead, chelating and/or stabilizing agents are suitable additional functional ingredients which may be included in the methods of generating the performic acid and/or added after completion of the reaction forming the performic acid compositions prior to use, and/or during generating a use solution of the performic acid compositions.

In some aspects, the present invention requires acidic conditions. Preferably, in some embodiments, the pH of the system does not exceed 7. More preferably, the pH does not exceed 5. More preferably, the pH does not exceed 3. Still more preferably, the pH does not exceed 2.

Beneficially, the performic acid compositions generated according to the invention may be further combined or produced in combination with additional chemistries, such as for example equilibrium chemistries, such as additional peroxycarboxylic acid compositions.

Eliminated Functional Ingredients

Unlike conventional equilibrium based performic acid compositions, the compositions disclosed herein are formed from a non-equilibrium reaction. Further, the composition disclosed herein can be used immediately after generation. Thus, many of the additional ingredients required in equilibrium based compositions do not need to be included in the present compositions. In some embodiments stabilizing agents are preferred for certain compositions according to the invention and provide benefits. However, beneficially, the use of non-equilibrium chemistry according to the present invention optionally provides that the compositions can be free of, or substantially free of a stabilizing agent.

Stabilizing agents are commonly added to equilibrium performic acid compositions to stabilize the performic acid and hydrogen peroxide and prevent the decomposition of these constituents within the compositions. Various embodiments of the invention do not require the use of at least one or more of such stabilizing agents. Examples of stabilizing agents may include for example, surfactants, couplers, hydrotropes, acid catalysts and the like that are conventionally used in equilibrium performic acid compositions to stabilize and improve shelf life of the composition.

Further examples of stabilizing agents include, for example, chelating agents or sequestrants. Such sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid). Dipicolinic acid, 1-hydroxy ethylidene-1,1-diphosphonic acid (CH3C(PO3H2)2OH) (HEDP) are further example of stabilizing agents.

Additional examples of stabilizing agents commonly used in equilibrium chemistry to stabilize the performic acid and hydrogen peroxide and/or prevent the premature oxidation of the composition include phosphonic acid or phosphonate salt. Phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are well known as used stabilizing agents.

Exemplary commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), (N[CH$_2$PO$_3$H$_2$]$_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM. Further exemplary sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof. Still further sequestrants include polycarboxylates, including, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

Further, unlike conventional equilibrium based performic acid compositions, the present compositions can also be free of, or substantially free of surfactants. This is especially advantageous for compositions incorporating C5 to C18 peroxycarboxylic acids. That is, under perhydrolysis conditions, the C5-C18 peroxycarboxylic acid anions generated are water soluble. If the anions (e.g. peroxycarboxylic acid-forming compositions) are acidified for end use applications, the concentrations of peroxycarboxylic acids are below the water solubility limit of the peroxycarboxylic acids. Thus, couplers are not needed to couple the peroxycarboxylic acids in solution.

Additional Functional Ingredients

The compositions may also include additional functional ingredients. Additional functional ingredients suitable for use in the present compositions include, but are not limited to, acidulants, hydrotropes, dispersants, antimicrobial agents, optical tracers, solidification agent, aesthetic enhancing agent (i.e., colorant (e.g., pigment), odorant, or perfume), among any number of constituents which can be added to the composition. For example, suitable functional ingredients for various embodiments of the invention are hydrotropes, which may be desired for producing clear compositions or dispersants which are more efficient in producing homogeneous dispersions. Such adjuvants can be preformulated with the present compositions or added to the compositions after formation, but prior to use. Additionally, the present invention may include optional use of an acidity source either prior to the reaction or after the reaction's completion. As one skilled in the art would appreciate, use of an acid source prior to the reaction would increase the kinetics of the reaction and/or decreases the heating requirements, while the addition of an acid source post-reaction would drive the pH of the performic acid below the pKa of formic acid, thus increasing the stability of the composition. The compositions can also contain any number of other constituents as necessitated by the application, which are known and which can facilitate the activity of the present compositions.

Exemplary additional functional ingredients are disclosed in U.S. patent application Ser. No. 14/972,308 titled "Mixture Comprising Formic Acid Hydrogen Peroxide, Methods of Generating the Mixture, and Use of the Mixture for Antimicrobial Control" and Ser. No. 14/973,389 titled "In Situ Generation of Peroxyformic Acid through Polyhydric Alcohol Formate", each of which are herein incorporated by reference in their entirety.

In some embodiments, the performic acid compositions may include a stabilizing agent, which is not required for formulation of the performic acid compositions but may provide benefits for mixed performic acid compositions according to the invention. Such stabilizing agents including for example phosphonic acids and phosphonate salts such as HEDP, may be particularly suitable for use of the mixed performic acid compositions for use at high temperatures.

System for Making On-Site Performic Acid Compositions

In some aspects, the present invention relates to an adjustable generator apparatus or system for on-site generation of performic acid chemistries. The system produces performic acid forming compositions according to the disclosure presented herein. Performic acid forming compositions refer to the generation of performic acid (including mixed peracids comprising performic acid) in situ, in a non-equilibrium reaction.

In some aspects, the system for on-site generation of performic acid forming compositions may comprise, consist of and/or consist essentially of an apparatus including an inlet (or at least two inlets, or at least three inlets), a length of pipe, at least one heating device, and an outlet for dosing the generated chemistry from the length of pipe. In some aspects, the system may optionally include a mixer or mixing device within the length of pipe. In some aspects, the system may optionally include a cooling segment or loop. In some aspects, the system may optionally include at least one measurement device. In some aspects, the system may optionally include a control system. In some aspects, the system may optionally include safety devices.

Inlet

In some aspects, the invention consists of at least one inlet through which reagents are supplied to the length of pipe. In embodiments where only one inlet is present, the reagents are mixed prior to the inlet.

In further embodiments of the invention, at least two inlets are present, wherein each reagent enters the length of pipe via its individual inlet. In such embodiments having at least two inlets, the inlets may be separated by a length of pipe to allow sequential addition of the reagents. In some embodiments a first inlet doses formic acid (and blends of formic acid) to the reactor and a second inlet doses the hydrogen peroxide source to the reactor. In such an embodiment, one of the inlets may further be used to flush the system with water. In embodiments of the invention, the formic acid source and the oxidizing agent are introduced to the length of pipe in a ratio from about 1:1 to about 5:1, preferably from about 2:1 to about 40:1, and preferably about 20:1.

In further embodiments of the invention, at least three inlets are present, wherein each reagent enters the length of pipe via its individual inlet as well as a third inlet used for flushing the system with water, adding a corrosion inhibitor, biocide or additional functional component to the length of pipe. In such embodiments having at least three inlets, the inlets may be separated by a length of pipe to allow sequential addition of the reagents. In some embodiments a first inlet doses formic acid to the reactor, a second inlet doses the hydrogen peroxide source to the reactor, and a third inlet allows water to be flushed through the system and/or provides additional components such as a corrosion inhibitor or biocide. Alternatively, a third inlet may be placed upstream of the first and/or second inlets so as to flush the inlets and the remainder of the system with water. In still further embodiments of the invention, at least four inlets are present, wherein each reagent enters the length of pipe via its individual inlet as well as a third inlet used for an additional peroxycarboxylic acid, and a fourth inlet used for flushing the system with water, adding a corrosion inhibitor, biocide or additional functional component to the length of pipe. In such embodiments having at least four inlets, the inlets may be separated by a length of pipe to allow sequential addition of the reagents.

In embodiments of the invention, the formic acid source and the oxidizing agent are introduced to the length of pipe in a ratio from about 1:1 to about 5:1, preferably from about 2:1 to about 40:1, and preferably about 20:1.

In a further aspect of the invention, the inlet temperature is approximately that of ambient temperature. However, as one skilled in the art would appreciate, a higher inlet temperature would reduce or eliminate the power required for heating and therefore reduce the risk of exceeding the decomposition temperature of the performic acid. In some aspects, the inlets may have different temperatures. For example, in embodiments where the formic acid and the hydrogen peroxide source are dosed to the system via separate inlets, the formic acid source inlet may have a higher inlet temperature than the hydrogen peroxide inlet.

According to the embodiments of the invention, flow direction through the system may be upward, downward, or lateral. However, as one skilled in the art would appreciate, flow direction may be dependent on the process and stream variables such as density, temperature, and pressure, as well as external mechanical considerations such as pumping power. In a preferred embodiment of the invention the second inlet which doses oxidizing agent to the system has a downward flow.

In a further aspect of the invention, the inlets may need to undergo degasification in order to remove dissolved gases from the liquid streams. As one skilled in the art would appreciate, degasification may need to occur for a number of reasons and without seeking to be limited to a particular theory of invention, gasification may occur in this application to remove dissolved gases from liquids that are possibly air- or -oxygen sensitive or to avoid cavitation of pumping systems in a downstream process.

In some embodiments of the invention, dilution of the reagents does not occur.

Length of Pipe

In some aspects of the invention, the reaction occurs within a length of pipe which meets the hydraulic requirements of the performic acid reaction kinetics. As referred to herein, the pipe refers generally to the length of a body within which the reaction occurs and is contained. Pipe should be understood to include a length of tubing or other receptacle suitable for containing the flow of the reaction for the performic acid reaction kinetics according to embodiments of the invention. Although not intending to be limited by a particular theory of the invention, the kinetics of the reaction according to the invention are pH, concentration, flow rate, and/or temperature dependent, and the reaction begins producing yield in the order of seconds to minutes. In some aspects of the invention, the reaction can produce at least about 2% performic acid instantaneously, at least about 4% performic acid within 1 minute, and at least about 8% performic acid within 2 minutes, and at least 15% performic acid within 30 minutes. Although not intending to be limited by a particular theory of the invention, the kinetics of the reaction according to the invention are pH, concentration, flow rate, and/or temperature dependent, and the reaction can reach maximum yield in the order of seconds to minutes. In some aspects the reaction can reach maximum performic acid yield within about 15 seconds, within about 30 seconds, within about 1 minute, or within about 2 to about 5 minutes.

The length of pipe may be designed in a variety of ways, including for example shape, size, temperature, and material. According to an embodiment of the invention, the length of pipe may be of a given inner diameter and is constructed of a material that is not readily corroded and/or damaged by the presence of formic acid, hydrogen peroxide, and/or performic acid(s). According to further embodiments, the length of pipe is constructed of a material that is not readily corroded and/or damaged by the presence of formic acid, hydrogen peroxide, performic acid(s), additional peracids and corresponding carboxylic acids, and/or additional functional ingredients, such as optional stabilizers and additional functional ingredients within the formulation for generating the performic acid.

In some embodiments, the length of pipes do not include for example copper, chromium, brass, and/or iron. Certain varieties of stainless steel are also to be avoided, for example, SS304. In a preferred embodiment of the invention, the length of pipe is constructed from SS316 and/or SS316L. In a preferred embodiment of the invention, the length of pipe is constructed from Polytetrafluoroethylene (PTFE) which is a synthetic fluoropolymer of tetrafluoroethylene. However, one skilled in the art will appreciate that other suitable materials are available.

In general the length of pipe is not effectively limited by pressure of the system due to the open system design of the generators according to embodiments of the invention. However, it is desirable that the pipe may be designed to accommodate the potential occurrence of a runaway reaction based upon the material of the pipe. Preferably the pipe is designed to accommodate pressures of at least 20 PSI, at least 40 PSI, at least 50 PSI, at least 100 PSI, at least 150 PSI, at least 500 PSI, at least 1000 PSI, at least 2000 PSI, or greater, including all ranges therein. In an aspect, as one skilled in the art will ascertain, the pressure of the system is controlled so as not to exceed the burst pressure of any material employed for the length of pipe of the generator or apparatus of the invention. Beneficially, additional components of the generator or apparatus may optionally include pressure relief valves, rupture disks, or the like to control the pressure of the open system.

In some aspects of the invention, the flow through the pipe occurs at a rate of about 0.1 mL/minute to about 100 mL/min, preferably about 10 mL/min to about 50 mL/min, preferably about 20 mL/min to about 40 mL/min. In an aspect of the invention, higher flow rates can be achieved by employing the apparatuses in parallel. In an aspect of the invention, higher flow rates can be achieved by turbulent flow systems. However, in some aspects, laminar flow systems are provided and may be combined with a mixer or mixing device contained within the length of pipe. In an aspect of the invention, it is preferred that flow through the pipe has a laminar flow pattern, i.e., flow have a Reynolds number of less than about 2040 in order to allow for uniform heating.

In some embodiments, the length of pipes may be increased to enhance the residence time of the reaction for generating the peroxyformic acid in the generator according to the invention. In an exemplary embodiment, the length of the pipes may be at least 1 foot, at least about 10 feet, at least about 50 feet, or at least about 90 feet. In an embodiment a coiled length of pipes provides for increased length and residence time for the reaction without occupying additional space for the length of pipes of the generator. These and other modifications are included within the scope of the disclosure.

Heating Device

In an aspect of the invention, heat is provided to the system through the use of at least one heating device. In a further aspect of the invention, heat is provided to the system through the use of at least two heating devices. Suitable heating devices include for example, cartridge, heat exchanger, heat blanket, steam jacket, solar panels, steam preheat, an electrical source, a heat wrap, or combinations thereof, each of which may be referred to herein as heating device.

In a preferred embodiment of the system, heat is provided to the system in an amount sufficient to raise the temperature of the reagents to accelerate the reaction and to a temperature not exceeding the decomposition temperature of performic acid, or about 200° C. More preferably, heat is provided to the system in an amount sufficient to raise the temperature of the reagents to a temperature not exceeding 180° C. In an aspect, the temperature increase will increase the rate of reaction, however, as one skilled in the art will ascertain, the stability of the performic acid is not to be compromised by increasing the temperature, including at a temperature not exceeding 200° C.

In some aspects of invention, the location of the heating device(s) is within a section or sections of pipe. In some aspects, the location of the heating device(s) is wrapped in insulation to eliminate the amount of heat lost to the environment, which may be on the inside and/or outside of the length of pipe. In such aspects, the insulation heating device may span all or a portion of the length of pipe.

In a preferred aspect, a heating device includes a cartridge located within the length of pipe. Such cartridge has a diameter less than the inner diameter of the pipe. According to a preferred embodiment of the invention, it is preferable to maintain the difference between the cartridge's diameter and the pipe's inner diameter less than about 5 inches, more preferable less than about 3 inches, and more preferably less than about 1.75 inches. Furthermore, the system possesses a given cross sectional area that is available for heat transfer, defined as the inner cross sectional area of the pipe minus the cross sectional area of the cartridge heater. However, one skilled in the art will appreciate that the optimal area available for heat transfer will depend on the temperature of the inlet(s), flow rate, heater length, etc. Although not intending to be limited by a particular theory of the invention, a larger cross sectional area is viable with a lower flow rate because the rate of heat transfer is lower, resulting in a lower temperature at the surface of the cartridge heater. In a further embodiment of the invention, heaters may be employed in series or in parallel in order to minimize the heater's temperature. In a further embodiment of the invention, the heat provided to the system is controlled via an electronic control system.

In some aspects of the present invention, wherein the heating device is a cartridge, the available volume of the pipe is affected. The available volume is thus defined as the volume held within the pipe at a given time minus the volume occupied by the heating cartridge. In a preferred embodiment, the volume of the system is increased by employing systems in parallel rather than increasing pipe size and or volume.

In a further aspect of the invention, uniform heating of the reagents within the length of pipe is desired, such uniform heating is influenced by the radial distance from the outside of the heater surface to the inner surface of the pipe, where a larger distance leads to a higher gradient, and the length of the heating zone, where longer contact with heater leads to a lower gradient. As one skilled in the art will appreciate, these influences have inverse effects on the heat gradient and will thus appreciate the weighing of these influences when determining the dimensions of the heating devices.

In a further aspect of the invention, uniform heating of the reagents within the length of pipe is not feasible and/or desired. In such embodiments, staged heating may be employed such that in a first section of the length of pipe the temperature of the reagent(s) is increased at a desired increment (e.g. 5-10 degrees C.), thereafter in a second section of the length of pipe the temperature of the reagent(s) is increased at a desired increment (e.g. 5-10 degrees C.), and so on.

In some aspects of the invention, the power required by the heating device and accompanying pumps preferably does not exceed about 100 watts for flow rates of 50 mL/min. More preferably, the power does not exceed 80 watts and more preferably, the power does not exceed 50 watts.

Heating can also be controlled, irrespective of the power of the heater, through control cycles that involve cycles of time where the heater is on for cycles of time. In an aspect, the controlled cycles may include the heater being on for about 10-100% of the cycle of the generator. In some embodiments, cycles of time can be from about 2 seconds to about 100 seconds. In another aspect, heating can also be controlled by PID loops with proportionality constants directly correlating to the flow rate. These and other modifications are included within the scope of the disclosure.

Outlet

In a preferred aspect of the present invention, an outlet is present. In an aspect of the invention the outlet provides the performic acid chemistries to a downstream process as desired by the controller and/or user. In an aspect, the outlet provides the performic acid chemistries to a storage reservoir. In an aspect, the outlet provides the performic acid chemistries to a cooling system. In an aspect of the invention, the concentration of the performic acid at the outlet is at least 1 wt-%, more preferably at least 5 wt-% at the outlet.

Mixer

In a preferred aspect of the present invention, at least one mixer or mixing device is present within the length of pipe. The mixed or mixing device can include any suitable forms for the mixer or mixing device, such as an impeller or any type of static mixer. In some aspects, the mixer or mixing device is present in the length of pipe at a point downstream from the addition of the hydrogen peroxide source. In such an embodiment the combined reagents of at least the formic acid and the hydrogen peroxide source are combined via mixing. As one skilled in the art will ascertain, under laminar flow conditions it is desirable to have a mixer or mixing device. However, a system designed to provide turbulent flow does not require a mixer or mixing device. In some embodiments, either a laminar or turbulent flow systems employs a mixer or mixing device.

Cooling System

In another aspect of the invention, the system may include a cooling system or a cooling loop/segment on the reaction vessels. A cooling system may be in combination with a safety mechanism and/or a measurement device of the system. It may be desirable to have components of the system under temperature controls. As one skilled in the art will appreciate, exothermic reactions may degrade the reagents according to the generation of the performic acid compositions of the invention. In an aspect, the cooling system stabilizes the performic acid composition and thereby increases shelf-life by lowering the temperature to a temperature to that of freezing or below freezing. In addition, according to an embodiment of the invention, the system has at least one mechanism to cool components of the system. Multiple cooling mechanisms may be used in either series or parallel. Such mechanisms may include, for example, a quenching mode, increased surface area, cooling jacket, venting systems, cold finger, and the like. In a further aspect of the invention, the outlet of the performic acid(s) is cooled by using heat exchange, refrigeration sleeve, blower, cooled vessel, etc.

Measurement Devices

In some aspects of the disclosure, the system for on-site generation of performic acid forming compositions may include at least one measurement device or a plurality of measurement. Such measurement devices are those suitable to measure one or more reaction kinetics or system operations for the generation of performic acid forming compositions, including for example devices to measure conductivity, weight, flow (e.g. flow meters or switches), pH, pressure, temperature and combinations thereof. Such measurement devices may measure the system's inlets, piping, outlets, etc.

Examples of additional suitable measurement devices include, for example, conductivity sensors, thermometers, out of product alarms, peroxide monitors, IR/UV/VIS spectroscopy, NMR and pressure switches. For example, in an embodiment of the invention, temperature is monitored a various points in the apparatus to ensure consistent heating at a temperature not exceeding the flash point of the performic acid. Additionally, in an embodiment of the invention pressure is monitored to ensure there is not an occurrence of a "runaway reaction." This pressure monitoring could be accomplished by use of a differential pressure sensor within a feedback control loop, wherein in a pressure reading exceeding a set point would cause a safety release valve and/or rupture disk to be employed or venting to occur.

In another embodiment of the disclosure, temperature is monitored for indication of a run-away reaction. Temperature probes can be placed upstream and downstream of the reaction. If the downstream temperature is higher than the upstream temperature then run away reaction has occurred.

In a further embodiment of the disclosure, flow rate is monitored with either a pressure sensor or an orifice plate/meter. Furthermore, conductivity may be monitored to determine the concentration of products in the stream and/or the concentration of the performic acid at the outlet. In a further embodiment, generation rates, temperatures, and concentrations can all be optimized via monitoring systems and/or controllers. Additionally, an embodiment of the invention would allow for rinsing of the apparatus so that residual chemistry does not remain in the system.

A further suitable measurement device is an automatic titrator to measure the PFA active and Peroxide residual, such as disclosed in U.S. Pat. No. 8,980,636, which is incorporated herein by reference. Still further examples of suitable measurement devices are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

Control System

In some aspects, the system for making on-site performic acid chemistry formulations further comprises an optional controller or software platform. The software platform provides a user or system to select a generation mode for a desired performic acid formulation for on-site generation. As a result, use of the system for on-site performic acid chemistry generation provides significant user flexibility to generate chemistries for particular user-identified purposes. For example, the controller or control software for operation of the system may permit a user or system to select both the performic acid formulation and the desired volume and dosage concentration of the formulation for on-site generation. In a further aspect, the control software may determine the timing, sequencing and/or selection of feeding raw materials (e.g. reagents) into the system, mixing time and total reaction time required for production of the user- or system-selected performic acid formulation. In a still further aspect of the invention, the control system includes the above described measurement devices.

According to the invention, the controller may further include a mechanism for manually starting/stopping any of the same functions, including for example a manual switch panel for the same. In addition to manual controls, such as a manual switch panel, the controller preferably has buttons or other means for selecting particular embodiments according to option displayed by the control software platform. An embodiment of the controller may further include a display screen to assist a user in selecting a generation mode for a desired performic acid formulation and any other options for user selection as one skilled in the art will ascertain based upon the description of the invention. Concomitant with the control software are user-friendly instructions for use displayed on the display screen (or the like).

In an aspect of the invention, the control software utilizes a control software algorithm to maximize on-site active chemistry yield and provide safe operating conditions for the reactor vessel(s) of the system. The control software permits user-identified chemistry production to be run in one or multiple reaction vessels and to properly sequence reactions to obtain active chemistries.

In an aspect of the invention, the control software controls the temperature of the reaction to form the peroxyformic acid, namely controls the heating device of the on-site generator.

Examples of suitable controllers are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

In another aspect of the invention, the system may include a data output means for sharing information related to the performic acid forming compositions and/or performic acid formulations generated according to the system. For example, an information backbone may be used to both collect and disseminate data from the process of generating the performic acid formulations including, for example, composition consumption, dispensing or usage, and additional formulation production-related data. Such data may be generated in real-time and/or provided in a historical log of operational data detectable or storable by a user or system. In an embodiment of the invention a user or system is able to monitor usage and performance, including for example, chemistry dispensing, managing chemistry distribution to various point-of-use applications, communication with system operators to control and monitor chemistry dispensing, allocation and/or formulation and the like. According to an additional embodiment of the invention, a user or system is able to control systems, including program systems, remotely. Control systems also include safety shut off of the heater and pumps at no flow and shut offs when monitoring devices indicate a run-away reaction.

According to an aspect of the invention, any system operations suitable for use with the invention may be controlled and/or monitored from a remote location. Remote system operations control and/or monitoring may further include the system updates and/or upgrades. According to an aspect of the invention updates and/or upgrades to system operations may be downloaded remotely. These and other embodiments of data output means, information sharing, remote system operations and the like, which may be adapted for use with the present invention, are further described, for example, in U.S. Pat. Nos. 7,292,917, 6,895,307, 6,697,706 and 6,377,868 and U.S. Patent Publication Nos. 2005/0102059, 2005/0065644, 2004/0088076, 2003/0195657 and 2003/0195656, which are hereby expressly incorporated by reference including, without limitation, the specification, claims, and abstract, as well as any figures, tables, or drawings thereof.

In another aspect of the invention, the data output for sharing information related to the compositions according to the system may coordinate multiple systems on at a single site. According to this embodiment of the invention, information sharing between the multiple systems may take places place using any communications network capable of coupling one or more systems according to the present invention, including for example, using a server computer and a database.

Safety Devices

In some aspects of the invention, the system may include a variety of safety mechanisms. Exemplary on-site safety feedback mechanisms for a system are disclosed in further detail in U.S. Patent Publication No. 2009/0208365, which is hereby expressly incorporated by reference including, without limitation, the specification, claims, and abstract, as well as any figures, tables, or drawings thereof. Various safety mechanisms can measure pressure, temperature, difference in pressure, difference in temperature, or a combination thereof and provide a perceptible signal if one or more of these increases above a predetermined level. In an aspect, the level of pressure, temperature, difference in pressure, difference in temperature, or a combination thereof at which safety system provides a perceptible signal can be selected to allow intervention to avoid undesirable or unsafe conditions. In a further aspect of the invention, the system is designed to accommodate at least 5 times the pressure of the system (i.e. design pressure), more preferably at least 3 times the pressure of the system, and more preferably at least 1.5-2 times the pressure of the system. In a further aspect, the system is designed for explosion safety ratings, such as for example, according to the American Petroleum Institute (API). In a further aspect of the invention, the system may include pressure relief valves and/or rupture discs to control the pressure of the system.

Illustrated Embodiments

According to an embodiment of the invention, as shown in FIG. 1, a user or process controller input selects both the performic formulation and the flow rate and such input information is loaded into the system. Control software, including a software algorithm, may be used to calculate the flow rates required for the particular concentration. Raw materials are fed into the system under controlled flow rates and reaction times.

As shown in the exemplary and non-limiting FIG. 1, a user or process controller input (e.g. peracid and volume selection) is provided, and an adjustable biocide formulator system according to the invention is employed to provide raw materials (reagents) to feed a length of pipe under heated conditions which are controlled reaction conditions. The depicted system may employ a variety of measurement devices providing feedback to the system. Measurement devices according to the invention may include devices suitable to measure one or more reaction kinetics or system operations for the generation of performic acid forming compositions, including for example, devices to measure conductivity, weight, flow, pH, pressure, temperature and combinations thereof. A further suitable measurement device is an automatic titrator to measure the PFA active and Peroxide residual, such as disclosed in U.S. Pat. No. 8,980, 636, which is incorporated herein by reference. Such measurement devices may measure the system's inlets, pipes, outlets, heating devices, etc. Exemplary measurement devices may include the monitoring and reporting of the temperature and pressure of the length of pipe, the temperature and pressure of the materials at the inlet(s), the temperature and pressure of the materials at the outlet(s), and flow rate. Additional measurement devices may control: the flow rate; pH of raw materials and solutions in reaction; and the like. As one skilled in the art will ascertain, such regulators, measurement devices, sensors etc. are well known and not intended to limit the embodiments of the present invention.

In addition, measurement devices may be used to activate alarms indicating the system and/or methods of generating the performic acid forming compositions are outside of desirable ranges; for example, measurement devices may be used to generate out of product alarms (e.g. indicating a raw starting material is 'low' or out of product entirely). An exemplary measurement device for such an alarm would measure the availability of a particular raw material (premix or the like) from the volume of such raw material in a drum.

Optionally, for generation of a performic acid formulation (as opposed to the anion peroxycarboxylic acid forming compositions), the stability of the reaction intermediates may be enhanced by adding an acid or aqueous acidic solution. The system provides the user or process controller the desired performic acid formulation for use in a cleaning process, including without limitation, antimicrobial, bleaching, and sanitizing and/or anti-scaling applications. In addition, various data output and information sharing methods may optionally be employed according to the methods and systems of the invention.

Figure 2:
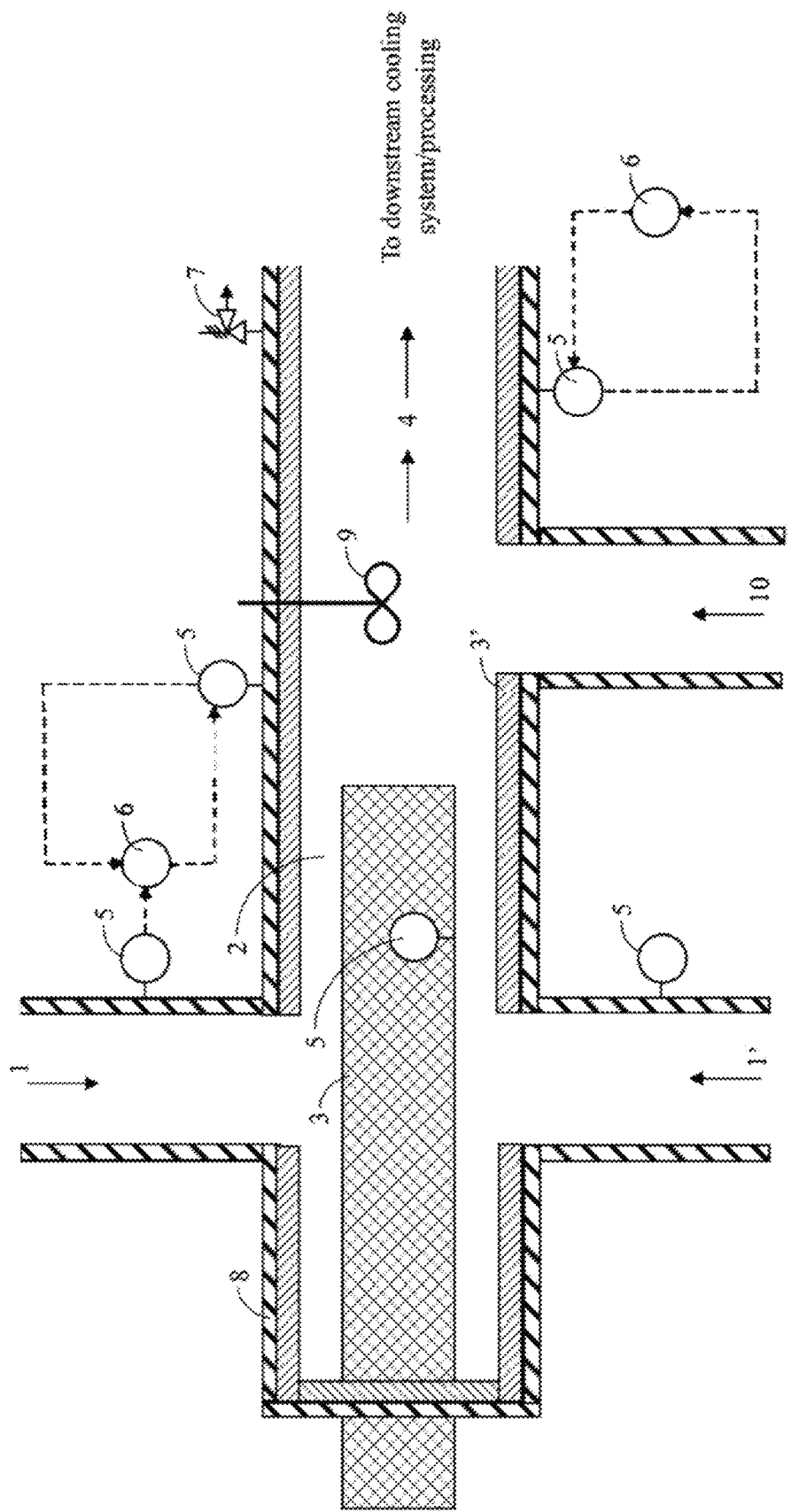
FIG. 2 shows diagram an exemplary embodiment of an adjustable biocide formulator apparatus according to the invention.

According to an embodiment of the invention shown in FIG. 2, reagents enter the length of pipe 2 through at least three depicted inlets 1, 1', 10. In an aspect, reagents include formic acid source and oxidizing agent. In a further aspect, an inlet is employed for flushing a system with water as needed. In an exemplary embodiment depicted by FIG. 2, a formic acid source is added at 1 or 1' (and a water flush is suitable for use at 1' or 1), and an oxidizing agent is added at 10. Such reagents are then contacted with at least one heating device 3, 3', which catalyzes the reaction of the performic acid source and the oxidizing agent to form the desired product. As depicted, the heating device is shown in distinct forms, including a heating cartridge 3, which penetrates through one end of the length of pipe and is disposed through at least a portion of the inner diameter of the pipe 2. An additional heating device is shown 3' as an insulating heater to at least a portion of the length of pipe. Without being limited according to the depicted embodiments, the insulating heater 3' could in the alternative or addition be wrapped around the outside of the pipe 2 (e.g. on the outside of the insulation of the pipe 8). Further depicted in the non-limiting depicted embedment are various optional measurement device(s) 5 which may be in connection with a control system 6. Any number of measurement device(s) 5 can be included in a system. Additionally the system may include safety devices 7 and/or insulation of the pipe 8 and/or a mixer 9. The mixed as depicted shows an impeller, however in many aspects a static mixer is employed. The depiction of 9 is a non-limiting depiction of a mixer. The performic acid forming compositions or performic acid compositions of the present invention are then supplied via an outlet 4 to either an optional downstream cooling system, storage reservoir or to the desired use.

Figure 3:
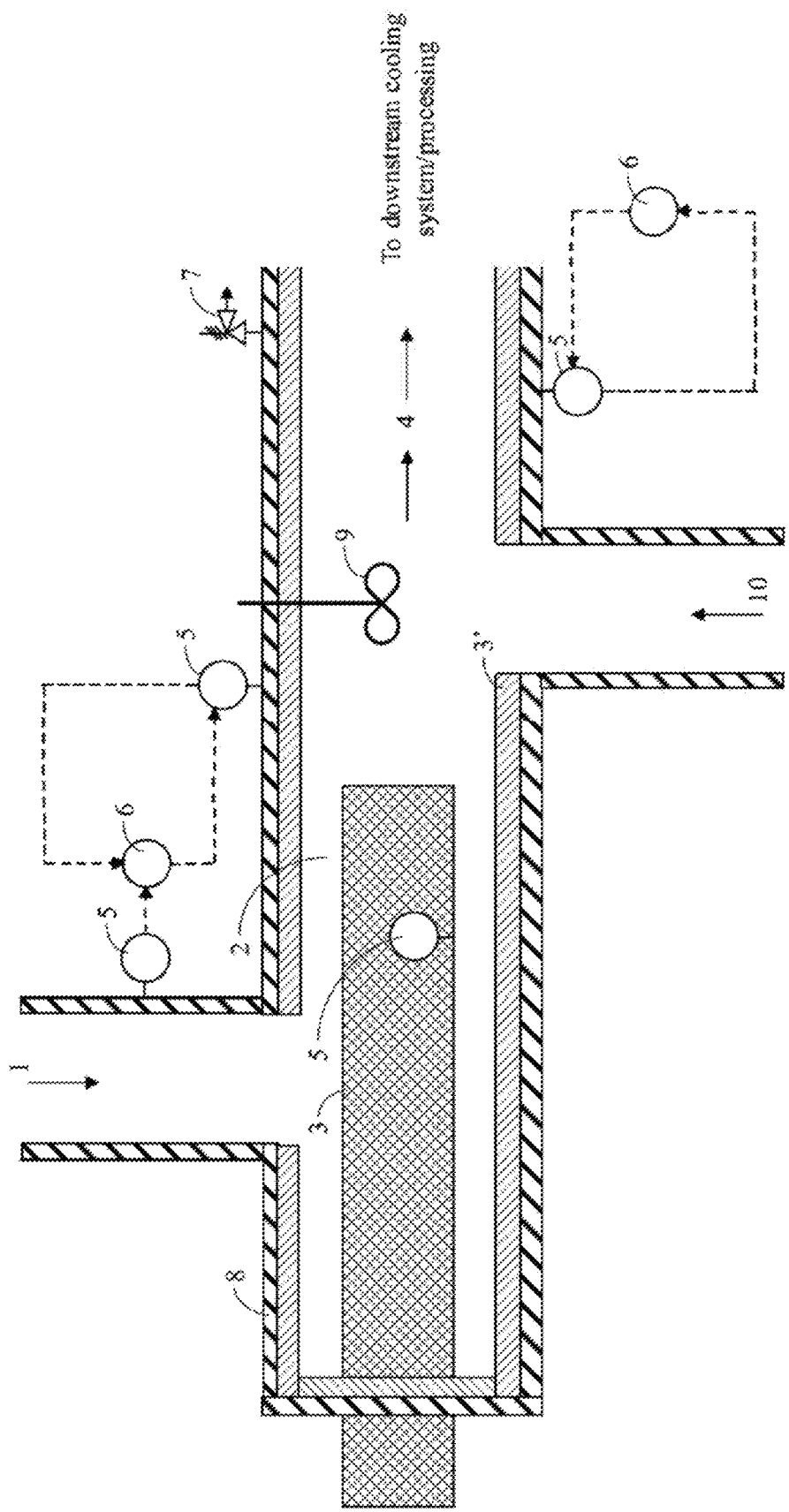
FIG. 3 shows diagram an exemplary embodiment of an adjustable biocide formulator apparatus according to the invention.

According to an embodiment of the invention shown in FIG. 3, reagents enter the length of pipe 2 through at least two depicted inlets 1, 10. In an aspect, reagents include formic acid source and oxidizing agent. In an exemplary embodiment depicted by FIG. 3, a formic acid source is added at 1 and an oxidizing agent is added at 10. Such reagents are then contacted with at least one heating device 3, 3', shown as a heating cartridge 3 penetrating through one end of the length of pipe 2 and is disposed through at least a portion of the inner diameter of the pipe 2. An additional heating device is shown 3' as an insulating heater to at least a portion of the length of pipe. Further depicted in the non-limiting depicted embodiment are various optional measurement device(s) 5 which may be in connection with a control system 6. Any number of measurement device(s) 5 can be included in a system. Additionally the system may include safety devices 7 and/or insulation of the pipe 8 and/or a mixer 9. The performic acid forming compositions or performic acid compositions of the present invention are then supplied via an outlet 4 to either an optional downstream cooling system, storage reservoir or to the desired use.

Figure 4:
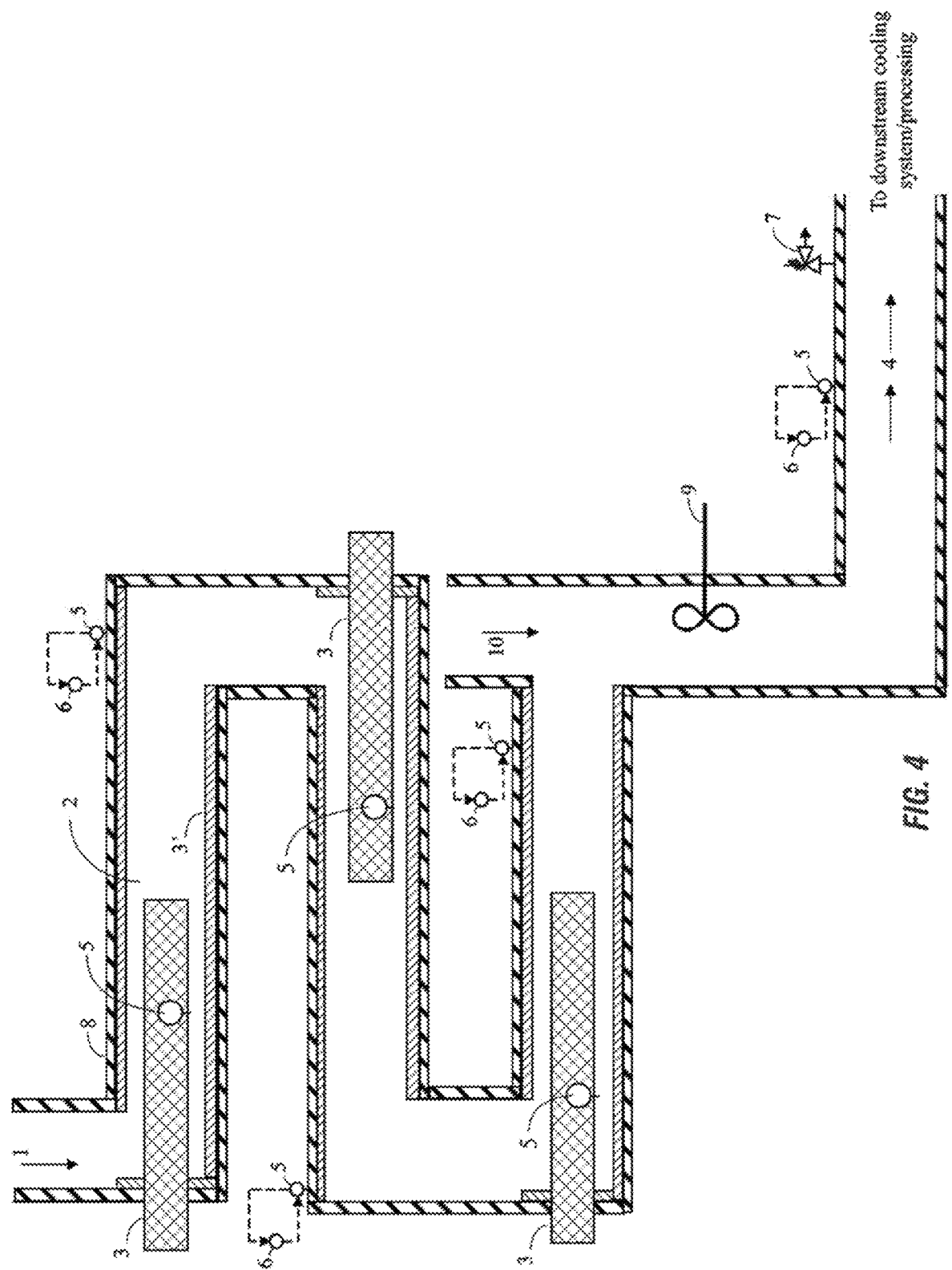
FIG. 4 shows diagram an exemplary embodiment of an adjustable biocide formulator apparatus according to the invention.

According to an embodiment of the invention shown in FIG. 4, a staged heating system is set forth for use according to the invention. A length of pipe 2 with at least two depicted inlets 1, 10 and provided to add reagents including formic acid source at inlet 1 and oxidizing agent at inlet 10. Such reagents are then contacted with at least one heating device 3, 3', shown as a heating cartridge 3 penetrating through one end of the length of pipe 2 and is disposed through at least a portion of the inner diameter of the pipe 2. As depicted a series of three staged heating portions of the length of pipe are provided along with an insulating heating layer 3' to at least a portion of the length of pipe. Further depicted in the non-limiting depicted embodiment are various optional measurement device(s) 5 which may be in connection with a control system 6. Any number of measurement device(s) 5 can be included in a system. Additionally the system may include safety devices 7 and/or insulation of the pipe 8 and/or a mixer 9. The performic acid forming compositions or performic acid compositions of the present invention are then supplied via an outlet 4 to either an optional downstream cooling system, storage reservoir or to the desired use.

Figure 9:
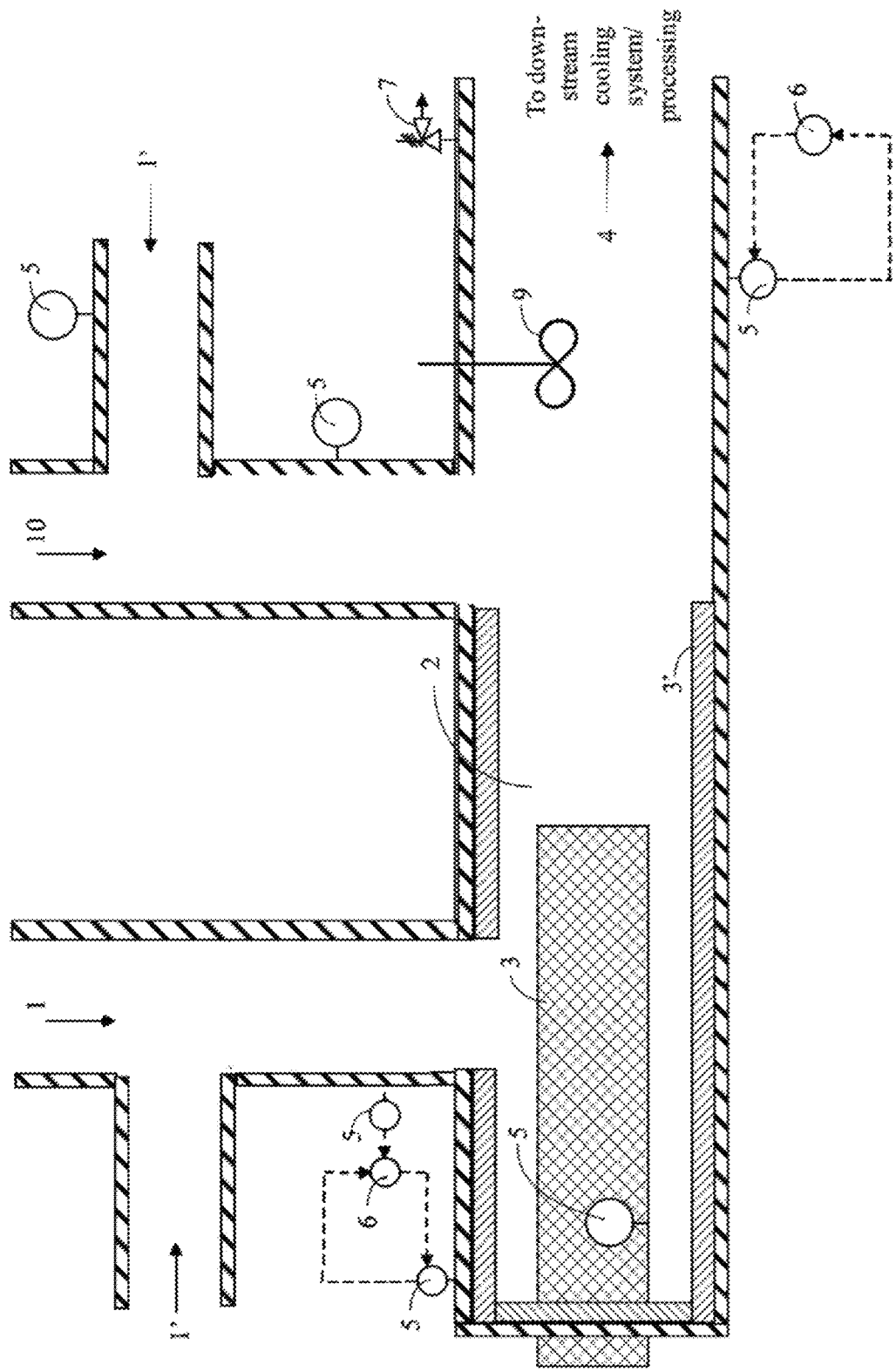
FIG. 9 shows a diagram of an exemplary embodiment of an adjustable biocide formulator apparatus according to the invention employing a downward flow of oxidizing agent for the generation of performic acid.

According to an embodiment of the invention shown in FIG. 9, reagents enter the length of pipe 2 through at least two depicted inlets 1, 10. In an aspect, reagents include a formic acid source and oxidizing agent. In an exemplary embodiment depicted by FIG. 9, a formic acid source is added at 1 and an oxidizing agent is added at 10. The formic acid source is then contacted with at least one heating device 3, 3', shown as a heating cartridge 3 penetrating through one end of the length of pipe 2 and is disposed through at least a portion of the inner diameter of the pipe 2. An additional exemplary heating device is shown 3' as an insulating heater to at least a portion of the length of pipe (which can further extend through or along any desired length of the pipe 2, and depicted in this figure as extending only a portion of the pipe 2). Further depicted in the non-limiting embodiment shown in the figure are water inlet 1' which may be used to flush the inlets 1, 10 and the length of pipe 2 with water. Additionally, the system may include various optional measurement device(s) 5 which may be in connection with a control system 6. Any number of measurement device(s) 5 can be included in a system and situated in various locations throughout. Further, the system may include safety devices 7 and/or insulation of the pipe 8 and/or a mixer 9 which can be included in a system and situated in various locations throughout. The performic acid forming compositions or performic acid compositions of the present invention are then supplied via an outlet 4 to either an optional downstream cooling system, storage reservoir or to a desired use. Beneficially, as depicted in FIG. 9, the generator employs a downward flow direction through the system to more readily contact the reagents for the in-situ reaction and enable the near instantaneous generation of performic acid. The depicted embodiment employing a downward flow direction of reagents, namely the oxidizing agent 10, adapts to the density of the reagent without requiring (or minimally requiring) external mechanical considerations such as pumping power. In a preferred embodiment of the invention, such as shown in FIG. 9, at least the second inlet (dosing the oxidizing agent 10) to the system has a downward flow.

Figure 10:
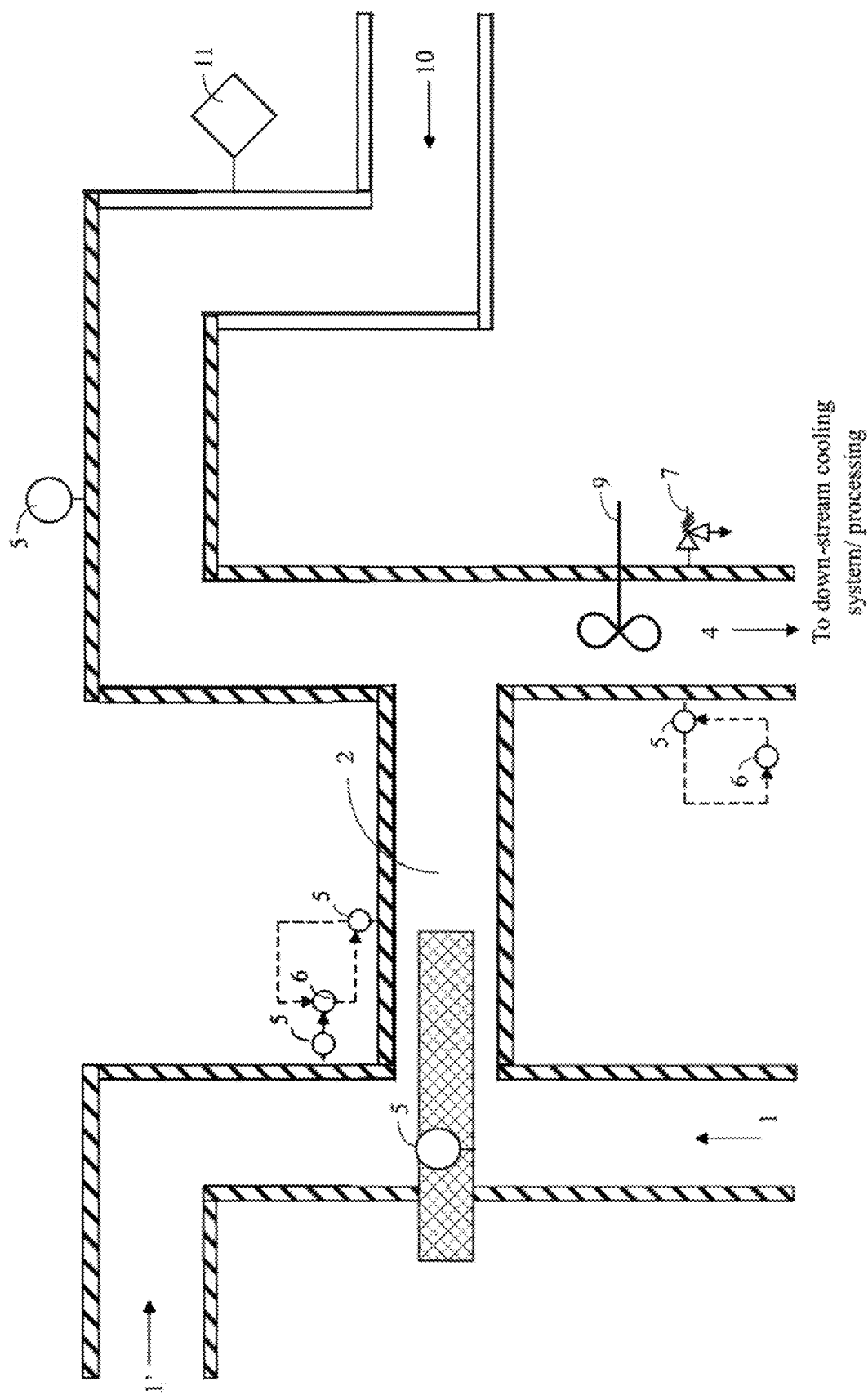
FIG. 10 shows a diagram of an exemplary embodiment of an adjustable biocide formulator apparatus according to the invention employing a downward flow of mixed reagents for the generation of performic acid.

According to an embodiment of the invention shown in FIG. 10, reagents enter the length of pipe 2 through at least two depicted inlets 1, 10. In an aspect, reagents include a formic acid source and oxidizing agent. In an exemplary embodiment depicted by FIG. 10, a formic acid source is added at 1 and an oxidizing agent is added at 10. The formic acid source is then contacted with at least one heating device 3, as shown as a heating cartridge 3 penetrating through one end of the length of pipe 3 and is disposed through at least a portion of the pipe 2. Further depicted in the non-limiting embodiment shown in FIG. 10 are water inlet 1' which may be used to flush the inlet 1 and the length of pipe 2 with water. Degasification may occur at 11 via any suitable method. Additionally, the system may include various optional measurement device(s) 5 which may be in connection with a control system 6. Any number of measurement device(s) 5 can be included in a system and situated in various locations throughout. Further, the system may include safety devices 7 and/or insulation of the pipe 8 and/or a mixer 9 which can be included in a system and situated in various locations throughout. The performic acid forming compositions or performic acid compositions of the present invention are then supplied via an outlet 4 to either an optional downstream cooling system, storage reservoir or to a desired use. Beneficially, as depicted in FIG. 10, the generator employs a downward flow direction through the mixer 9 to more readily contact the reagents for the in-situ reaction and enable the near instantaneous generation of performic acid. The depicted embodiment employing a downward flow direction of reagents, which are mixed in stream prior to reaching the mixer 9 adapts to the density of the reagents without requiring (or minimally requiring) external mechanical considerations such as pumping power.

Figure 12:
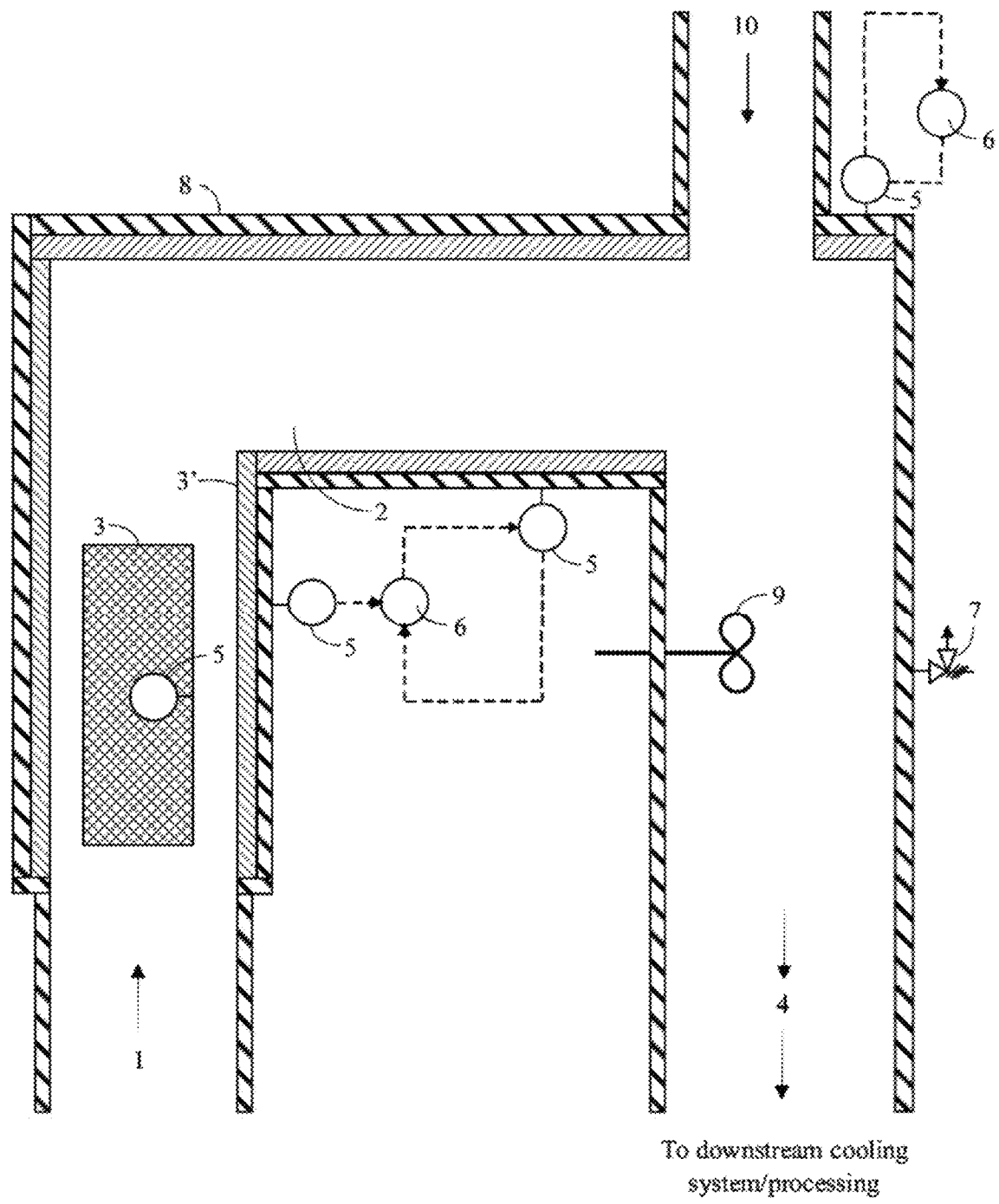
FIG. 12 shows a diagram of an exemplary embodiment of an adjustable biocide formulator apparatus according to the invention.

According to an embodiment of the invention shown in FIG. 12, reagents enter the length of pipe 2 through at least two depicted inlets 1, 10. In an exemplary embodiment depicted by FIG. 12, a formic acid source is added at 1 and an oxidizing agent is added at 10. The formic acid source is then contacted with at least one heating device 3 disposed through at least a portion of the pipe 2. Further depicted in the non-limiting embodiment shown in FIG. 12 is an outlet 4 to either an optional downstream cooling system, storage reservoir or to a desired use. Beneficially, as depicted in FIG. 12, the generator employs a downward flow direction of the oxidizing agent through the mixer 9 to more readily contact the reagents for the in-situ reaction and enable the near instantaneous generation of performic acid. The depicted embodiment employing a downward flow direction of the oxidizing agent reagents, which are mixed in stream prior to reaching the mixer 9 adapts to the density of the reagents without requiring (or minimally requiring) external mechanical considerations such as pumping power.

Although not depicted in every embodiment of the invention shown in the figures, various additional inlets may be present, such as for example water inlets to flush an inlet and/or a length of pipe 2 with water, or inlets for providing additional components include biocides and/or corrosion inhibitors, or still further additional inlets for providing additional peroxycarboxylic acids (such as those which may contain formic acid). Still further, degasification may occur at 11 via any suitable method within any of the depicted embodiments. Additionally, the systems may include various optional measurement device(s) 5 which may be in connection with a control system 6. Any number of measurement device(s) 5 can be included in a system and situated in various locations throughout. Further, the system may include safety devices 7 and/or insulation of the pipe 8 and/or a mixer 9 which can be included in a system and situated in various locations throughout. Each of these components can be included in the generator according to invention, including in configurations depicted in each of the figures. Still further, the various inlets and outlets can be configured with an upward or lateral flow and still others configured with a downward flow.

Performic Acid Compositions

In some embodiments, the system according to the present invention produces performic acid forming compositions or performic acid compositions for use in a variety of cleaning application. In some aspects, the present disclosure relates to performic acid forming compositions. That is, the compositions are capable of generating performic acids in situ, in a non-equilibrium reaction. Performic acid generally has the formula $CH_2O_3$.

In an embodiment of the invention the performic acid forming compositions comprise individual reagents combined according to the invention. These reagents are described herein individually and include at least source of formic acid and an oxidizing agent. Alternatively, as described herein, there may be benefits to providing the reagents in various premix formulations to decrease the number of reagents and/or increase the simplicity of the invention.

Methods for Making On-Site Performic Acid Compositions

In some embodiments, the methods according to the present invention for producing performic acid forming compositions or performic acid compositions comprise, consist of and/or consist essentially of providing a formic acid source, providing an oxidizing agent, contacting said formic acid source and oxidizing agent to form the reaction mixture, heating said reaction mixture at a given flow rate to form performic acid, and delivery said performic acid to a downstream process. In a further embodiment, the methods according to the present invention for producing performic acid forming compositions or performic acid compositions comprise cooling the performic acid. In a further embodiment, the methods according to the present invention for producing performic acid forming compositions or performic acid compositions comprise measuring variables including conductivity, temperature, product levels, concentration, IR/UV/VIS spectroscopy, pressure, flow rate, etc. In a further embodiment, the methods according to the present invention for producing performic acid forming compositions or performic acid compositions comprise controlling the system through use of a control system. In a further embodiment, the methods according to the present invention for producing performic acid forming compositions or performic acid compositions comprise employing safety devices.

Formic Acid Source

In an aspect of the invention, a formic acid source is provided to the system. The formic acid source used in the present methods can be provided in any suitable way. In some embodiments, before the contacting step, the formic acid can be provided in a composition that comprises formic acid, e.g., an aqueous solution that comprises formic acid and additional optional functional ingredients, such as a corrosion inhibitor. In other embodiments, before the contacting step, the formic acid can be provided in a composition that comprises a substance that generates formic acid upon contact with an aqueous composition. Any suitable substance that generates formic acid can be used in the present methods.

In an aspect, the formic acid source is an aqueous solution that comprises formic acid. In another aspect, the formic acid source is a salt of formic acid, such as formate, e.g., a sodium or ammonium salt of formate. In an aspect, the formic acid source is an ester alcohol, such as ethyl formate, propylene formate, glycerol formate, etc.

In an aspect, the formic acid source is a composition that comprises formic acid (or a salt of formic acid) and additional optional functional ingredients, such as a corrosion inhibitor. Beneficially, the formic acid and corrosion inhibitor systems provide a corrosion protected system. In such an embodiment, the concentration of the corrosion inhibitors will be less than 10% of the formic acid composition, preferably less than % of the formic acid composition. In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof.

In an aspect, the formic acid source is a composition that comprises formic acid (or a salt of formic acid) and additional percarboxylic acids and/or carboxylic acids, such as C1-C22 percarboxylic acids and/or carboxylic acids, preferably C5-C22 percarboxylic acids and/or carboxylic acids, to beneficially provide a blended formic acid composition to provide synergistic antimicrobial efficacy against microorganisms. In such aspects, a mixture of peroxyformic acid, and additional percarboxylic acids and/or carboxylic acids, such as peracetic acid or peroctanoic acid, such as disclosed in U.S. Pat. No. 5,314,687 which is herein incorporated by reference in its entirety, are provided. In such an aspect, the peracid mixture provides antimicrobial synergy. In an aspect, the synergy of a mixed peracid system allows the use of lower dosages of the peracids.

Oxidizing Agent

The compositions also include an oxidizing agent. The oxidizing agent may include a peroxide source. In an aspect, the hydrogen peroxide is 1-50% w/v hydrogen peroxide. Oxidizing agents suitable for use with the compositions include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4] \cdot 6H_2O$ (also called sodium perborate tetrahydrate); sodium peroxyborate tetrahydrate of the formula $Na_2B_2(O_2)_2[(OH)_4] \cdot 4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some embodiments, the oxidizing agent includes hydrogen peroxide, or a source or donor of hydrogen peroxide. In other embodiments, the oxidizing agent includes a peroxide source selected from a percarbonate, a perborate urea hydrogen peroxide, PVP-peroxides and mixtures thereof.

Additional Optional Components

In an embodiment, the reagents described herein (e.g. formic acid and an oxidizing agent) may be combined with additional optional components. In an aspect, the additional components can include a corrosion inhibitor. Corrosion inhibitors are additional molecules used in oil and gas recovery operations. Corrosion inhibitors that may be employed in the present disclosure are disclosed in U.S. Pat. No. 5,965,785, U.S. Patent Publication No. 2010/0108566, GB Patent No. 1,198,734, WO/03/006581, WO04/044266, and WO08/005058, each of which are incorporated herein by reference in their entirety.

In an aspect, the additional components can include an additional biocide. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions. In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention. In a preferred aspect, the additional biocide is Gluteraldehyde, THPS, quat amine, and/or TTPC.

In an aspect, the additional components can include a friction reducer. Friction reducers are used in water or other water-based fluids used in hydraulic fracturing treatments for subterranean well formations in order to improve permeability of the desired gas and/or oil being recovered from the fluid-conductive cracks or pathways created through the fracking process. Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Premix Formulations

In an embodiment, the reagents described herein (e.g. formic acid and an oxidizing agent) may be combined in a premix formulation to reduce the number of raw starting materials required for the methods and compositions and further simplify the methods of the invention. According to such an embodiment the providing of premix formulations ensures consistent and stable delivery of reagents.

Premix formulations suitable for use according to the invention may comprise, consist of and/or consist essentially of at least formic acid source, a combination of formic and other C2-C18 carboxylic acids and, an oxidizing agent and mixtures thereof.

As one skilled in the art will ascertain, the use of premixes employs additional functional ingredients for purpose of stabilizing the premix concentrate for use in the compositions and methods according to the invention. For example, hydrotropes, dispersing agents and/or other solvents may be desirable for maintaining the solubility and stability of a particular concentrated premix. The use of any couplers or dispersing agent (such as a surfactant) within a premix formulation is distinct from the use of surfactants in the conventional generation and storage of performic acid chemistries, wherein couplers are critical to establishing and maintaining a stable, clear solution of the generated performic acid chemistry.

According to the invention, the use of dispersing agents alone within a concentrated premix formulation does not stabilize the premix composition. Rather the dispersing agents are provided in an amount suitable for providing meta-stable performic acid compositions generated from the premix after acidification, before further dilution for application. The most efficient dispersing agents were found to be anionic surfactants, and this type of surfactant is known to have high foaming profile. For applications which involves mechanical actions (e.g. CIP sanitizing), the high foam property of the composition is undesirable. Thus, in addition to economic reason, it is preferred to use a minimum amount of the dispersing agent to achieve a meta-stable performic acid composition to meet the application of use requirements.

According to an embodiment of the invention less than about 10 ppm, preferably less than about 9 ppm, less than about 8 ppm, less than about 7 ppm, less than about 6 ppm, less than about 5 ppm, less than about 4 ppm, less than about 3 ppm, less than about 2 ppm, or less than about 1 ppm of a dispersing agent is included in the generated performic acid chemistry as a result of the use of a surfactant dispersing agent in a concentrated premix formulation according to the invention. This is distinct from the level of surfactants in use solutions of a traditional performic acid chemistry, where the amounts of surfactants are normally in excess of about 50 ppm, in excess of about 60 ppm, in excess of about 70 ppm, in excess of about 80 ppm, in excess of about 90 ppm, or in excess of about 100 ppm.

According to an embodiment of the invention, the use of a solvent (e.g. ethanol) is an efficient way to make a stable premix composition. Solvents suitable for the concentrated premix formulations according to the invention include, for example, organic solvents such as alcohol, ether or ketone. Preferably, the solvent is a water soluble alcohol, such as ethanol, methanol, propanol, isopropanol and/or butanol. As one skilled in the art will ascertain the various isomers of the solvents, including alcohols, are further included within the scope of the solvents suitable for use with the concentrated premix formulations of the invention.

Beneficially, the use of concentrated premix formulation still does not require the use of any chelators and/or stabilizers. As a result, regardless of whether individual reagents or concentrated premix formulations are utilized according to the invention, both the reagents and the performic acid compositions generated according to the invention provide sustainable chemistries as a result of the elimination of the use of various stabilizers and/or additional amounts of chemistry required to drive the formation of traditional performic acid chemistry. As a result of reduced input of reagents for the compositions according to the invention (e.g. resulting from the use of a non-equilibrium reaction) there is a significantly reduced waste stream (e.g. any reagents and/or percentage of composition not impacting the micro-efficacy of the compositions). Instead the present invention provides increased amounts of post-reaction products (e.g. performic acids) with decreased amounts of unreacted reagents.

In an aspect of the invention, a premix formulation may deliver the formic acid source and the oxidizing agent.

Suitable dispersing agents for use according to the concentrated premix formulations of the invention include polymers, surface active agents or any compounds which will help to achieve a meta-stable solution after the ester perhydrolysis through the interaction with the peroxy fatty acids generated through perhydrolysis. These may include, for example, sulfonated oleic acids (SOA), 1-octanesulfonic acid (NAS), sodium lauryl sulfonates (SLS) and the like. In another aspect a premix formulation includes an ester of a polyhydric alcohol and a carboxylic acid, an oxidizing agent and a solvent. Ethanol and methanol are examples of suitable solvents for use in stabilizing the concentrated premix formulation according to the invention. The use of the solvent in certain embodiments obviates the use of a dispersing agent for premix stability. However, in alternative embodiments a premix formulation may include an ester of a polyhydric alcohol and a carboxylic acid, an oxidizing agent, a dispersing agent and a solvent. Without wishing to be limited to a particular theory or mechanism of action of the invention, the combined use of a dispersing agent and a solvent within a concentrated premix formulation reduces the overall need for a surfactant dispersing agent in the premix composition.

Reaction Mixture Formation

According to an embodiment of the invention, the formic acid source and an oxidizing agent are combined to form a reaction mixture. In an embodiment of the invention, the formic acid source and an oxidizing agent are provided to the length of pipe. In an embodiment of the invention, the formic acid source and oxidizing agent are provided to a vessel located upstream of the inlet to the length of pipe and subsequently provided to the length of pipe. According to the embodiments of the invention, flow direction through the system may be upward, downward, or lateral. However, as one skilled in the art would appreciate, flow direction may be dependent on the process and stream variable such as density, temperature, and pressure, as well as external mechanical considerations such as pumping power. In a preferred embodiment of the invention the second inlet which doses oxidizing agent to the system has a downward flow. In a further aspect of the invention, the reaction mixture is not formed by a mechanical means of mixing. In an alternative embodiment of the invention, the reaction mixture is formed by a mechanical means of mixing, for example, such as an impeller, or the like as one skilled in the art will appreciate, for circulation within the reaction vessel, circulation pumps or be gravity-driven, employ additional holding vessels, reagent delivery sensors (e.g. proof of reagent and/or performic acid chemistry delivery sensor) or combinations of the same to meet the performic acid reaction kinetics of the system.

In an aspect of the invention, the timing of the reaction is dependent on the flow rate and/or flow direction of the reagents, the amount of heat transfer available, and the desired concentration of performic acid. Although not intending to be limited by a particular theory of the invention, the kinetics of the reaction according to the invention are pH, concentration, flow rate, and/or temperature dependent, and the reaction begins producing yield in the order of seconds to minutes. In some aspects of the invention, the reaction can produce at least about 2% performic acid instantaneously, at least about 4% formic acid within about 1 minute, and at least about 8% performic acid within about 2 minutes. In a preferred embodiment of the invention, the duration of the reaction is preferably less than about 1 hour, preferably less than about 30 minutes, preferably less than about 15 minutes, and preferably less than about 10 minutes. In a further aspect of the invention, the reaction is ran until completion, however as one skilled in the art can appreciate that there may be situations in which it may be desirable not to run the reaction to completion.

Heating of Reaction Mixture

In an aspect of the invention, the reaction mixture is heated within a length of pipe in order to effectuate the conversion of reagents to performic acid. In some aspects of the invention, the reaction occurs within a length of pipe which meets the hydraulic requirements of the performic acid reaction kinetics. Although not intending to be limited by a particular theory of the invention, the kinetics of the reaction according to the invention are pH, concentration, flow rate, and/or temperature dependent, and the reaction can reach maximum yield in the order of seconds to minutes. Although not intending to be limited by a particular theory of the invention, the kinetics of the reaction according to the invention are pH, concentration, flow rate, and/or temperature dependent, and the reaction begins producing yield in the order of seconds to minutes. In some aspects of the invention, the reaction can produce at least about 2% performic acid instantaneously, at least about 4% formic acid within about 1 minute, and at least about 8% performic acid within about 2 minutes. In some aspects the reaction can reach maximum yield within about 15 seconds, or within about 30 seconds, within about 1 minute, or within about 2 to about 5 minutes. The length of pipe may be designed in a variety of ways, including for example shape, size, temperature, and material. According to an embodiment of the invention, the length of pipe may be of a given inner diameter and is constructed of a material that is not readily corroded and/or damaged by the presence of formic acid, hydrogen peroxide, and/or performic acid(s). Such piping materials to be avoided include, for example copper, chromium, brass, and/or iron. Certain varieties of stainless steel are also to be avoided, for example, SS304. In a preferred embodiment of the invention, the length of pipe is constructed from SS316 and/or SS316L. However, one skilled in the art will appreciate that other suitable materials are available.

In some aspects of the invention, the length of pipe is limited by pressure of the system. For example, the pipe may be designed to accommodate the potential occurrence of a runaway reaction. Preferably the pipe is designed to accommodate pressures of at least 20 PSI, at least 40 PSI, at least 50 PSI, at least 100 PSI, at least 150 PSI, at least 500 PSI, at least 1000 PSI, or greater, including all ranges therein. In an aspect, as one skilled in the art will ascertain, the pressure of the system is controlled so as not to exceed the burst pressure of any material employed for the length of pipe of the generator or apparatus of the invention. Beneficially, additional components of the generator or apparatus may optionally include pressure relief valves, rupture disks, or the like to control the pressure of the system.

In some aspects of the invention, the flow through the pipe occurs at a rate of about 1 mL/minute to about 100 mL/min, preferably about 10 mL/min to about 50 mL/min, preferably about 20 mL/min to about 40 mL/min. In an aspect of the invention, higher flow rates can be achieved by employing the apparatuses in parallel. In an aspect of the invention, it is preferred that flow through the pipe has a laminar flow pattern, i.e., flow have a Reynolds number of less than about 2040 in order to allow for uniform heating.

In an aspect of the invention, heat is provided to the system through the use of a cartridge, heat exchanger, steam jacket, steam preheat, an electrical source, a heat wrap or combinations thereof, which may be referred to herein as heating device. In some aspects of invention, the location of the heating device within the section of pipe is further wrapped in insulation to eliminate the amount of heat lost to the environment.

In a preferred embodiment of the system, heat is provided to the system in an amount sufficient to raise the temperature of the reagents to accelerate the reaction and to a temperature not exceeding the decomposition temperature of performic acid, or about 200° C. More preferably, heat is provided to the system in an amount sufficient to raise the temperature of the reagents to a temperature not exceeding 180° C. In an aspect, the temperature increase will increase the rate of reaction, however, as one skilled in the art will ascertain, the stability of the performic acid is not to be compromised by increasing the temperature, including at a temperature not exceeding 200° C.

In a further aspect of the invention, a uniform heating of the reagents within the length of pipe is desired, such uniform heating is influenced by the radial distance from the outside of the heater surface to the inner surface of the pipe, where a larger distance leads to a higher gradient, and the length of the heating zone, where longer contact with heater leads to a lower gradient. As one skilled in the art will appreciate, these influences have inverse effects on the heat gradient and will thus appreciate the weighing of these influences when determining the dimensions of the heating devices. In an alternative aspect, a staged heating of reagents within the length of pipe is desired.

In some aspects of the present invention, wherein the heating device is a cartridge, the available volume of the pipe is affected. The available volume is thus defined as the volume held within the pipe at a given time minus the volume occupied by the heating cartridge. In a preferred embodiment, the volume of the system is increased by employing systems in parallel rather than increasing pipe size and or volume.

In some aspects of the invention, the power required by the heating device and accompanying pumps preferably does not exceed about 100 watts for flow rates of 50 mL/min. More preferably, the power does not exceed 80 watts and more preferably, the power does not exceed 50 watts.

Performic Acid Delivery

In a preferred aspect of the present invention, the performic acid is delivered to a downstream process via an outlet. In an aspect of the invention the outlet provides the performic acid chemistries to a downstream process as desired by the controller and/or user. In an aspect, the outlet provides the performic acid chemistries to a storage reservoir. In an aspect, the outlet provides the performic acid chemistries to a cooling system. In an aspect of the invention, the concentration of the performic acid at the outlet is at least 1 wt-%, more preferably at least 5 wt-% at the outlet.

Cooling of Performic Acid

In a further aspect of the invention, the performic acid is cooled via a cooling loop/segment. Such a cooling system may be in combination with a safety mechanism and/or a measurement device of the system. It may be desirable to have components of the system under temperature controls. As one skilled in the art will appreciate, exothermic reactions may degrade the reagents according to the generation of the performic acid compositions of the invention. In an aspect, the cooling system stabilizes the performic acid composition and thereby increases shelf-life by lowering the temperature to a temperature to that of freezing or below freezing. In addition, according to an embodiment of the invention, the system has at least one mechanism to cool components of the system. Multiple cooling mechanisms may be used in either series or parallel. Such mechanisms may include, for example, a quenching mode, increased surface area, cooling jacket, venting systems, cold finger, and the like. In a further aspect of the invention, the outlet of the performic acid(s) is cooled by using heat exchange, refrigeration sleeve, blower, cooled vessel, etc.

Measurement Devices

In a further aspect of the invention, the methods according to the present invention for producing performic acid forming compositions or performic acid compositions include measuring at least one value or a plurality of values. Such measuring is accomplished by the use of measurement devices. Such measurement devices are those suitable to measure one or more reaction kinetics or system operations for the generation of performic acid forming compositions, including for example devices to measure conductivity, weight, flow (e.g. flow meters or switches), pH, pressure, temperature and combinations thereof. Such measurement devices may measure the system's inlets, piping, outlets, etc.

Examples of additional suitable measurement devices include conductivity sensors, thermometers, out of product alarms, peroxide monitors, IR/UV/VIS spectroscopy and pressure switches. For example, in an embodiment of the invention, temperature is monitored a various points in the apparatus to ensure consistent heating at a temperature not exceeding the flash point of the performic acid. Additionally, in an embodiment of the invention pressure is monitors to ensure there is not an occurrence of a "runaway reaction." This pressure monitoring could be accomplished by use of a differential pressure sensor within a feedback control loop, wherein in a pressure reading exceeding a set point would cause a safety release valve to be employed or venting to occur. In a further embodiment of the invention, flow rate is monitored with either a pressure sensor or an orifice plate/meter. Furthermore, conductivity may be monitored to determine the concentration of products in the stream and/or the concentration of the performic acid at the outlet. In a further embodiment, generation rates, temperatures, and concentrations can all be optimized via monitoring systems and/or controllers. Additionally, an embodiment of the invention would allow for rinsing of the apparatus so that residual chemistry does not remain in the system. Still further examples of suitable measurement devices are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

Control System

In a further aspect of the invention, the methods according to the present invention for producing performic acid forming compositions or performic acid compositions includes controlling the method by use of an optional controller or software platform. The software platform provides a user or system to select a generation mode for a desired performic acid formulation for on-site generation. As a result, use of the system for on-site performic acid chemistry generation provides significant user flexibility to generate chemistries for particular user-identified purposes. For example, the controller or control software for operation of the system may permit a user or system to select both the performic acid formulation and the desired volume of the formulation for on-site generation. In a further aspect, the control software may determine the timing, sequencing and/or selection of feeding raw materials (e.g. reagents) into the system, mixing time and total reaction time required for production of the user- or system-selected performic acid formulation. In a still further aspect of the invention, the control system includes the above described measurement devices.

According to the invention, the controller may further include a mechanism for manually starting/stopping any of the same functions, including for example a manual switch panel for the same. In addition to manual controls, such as a manual switch panel, the controller preferably has buttons or other means for selecting particular embodiments according to option displayed by the control software platform. An embodiment of the controller may further include a display screen to assist a user in selecting a generation mode for a desired performic acid formulation and any other options for user selection as one skilled in the art will ascertain based upon the description of the invention. Concomitant with the control software are user-friendly instructions for use displayed on the display screen (or the like).

In an aspect of the invention, the control software utilizes a control software algorithm to maximize on-site active chemistry yield and provide safe operating conditions for the reactor vessel(s) of the system. The control software permits user-identified chemistry production to be run in one or multiple reaction vessels and to properly sequence reactions to obtain active chemistries.

Examples of suitable controllers are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

In another aspect of the invention, the system may include a data output means for sharing information related to the performic acid forming compositions and/or performic acid formulations generated according to the system. For example, an information backbone may be used to both collect and disseminate data from the process of generating the performic acid formulations including, for example, composition consumption, dispensing or usage, and additional formulation production-related data. Such data may be generated in real-time and/or provided in a historical log of operational data detectable or storable by a user or system. In an embodiment of the invention a user or system is able to monitor usage and performance, including for example, chemistry dispensing, managing chemistry distribution to various point-of-use applications, communication with system operators to control and monitor chemistry dispensing, allocation and/or formulation and the like. According to an additional embodiment of the invention, a user or system is able to control systems, including program systems, remotely.

According to an aspect of the invention, any system operations suitable for use with the invention may be controlled and/or monitored from a remote location. Remote system operations control and/or monitoring may further include the system updates and/or upgrades. According to an aspect of the invention updates and/or upgrades to system operations may be downloaded remotely. These and other embodiments of data output means, information sharing, remote system operations and the like, which may be adapted for use with the present invention, are further described, for example, in U.S. Pat. Nos. 7,292,917, 6,895, 307, 6,697,706 and 6,377,868 and U.S. Patent Publication Nos. 2005/0102059, 2005/0065644, 2004/0088076, 2003/0195657 and 2003/0195656, which are hereby expressly incorporated by reference including, without limitation, the specification, claims, and abstract, as well as any figures, tables, or drawings thereof.

In another aspect of the invention, the data output for sharing information related to the compositions according to the system may coordinate multiple systems on at a single site. According to this embodiment of the invention, information sharing between the multiple systems may take places place using any communications network capable of coupling one or more systems according to the present invention, including for example, using a server computer and a database.

Safety Devices

In a further aspect of the invention, the methods according to the present invention for producing performic acid forming compositions or performic acid composition include employing safety devices. Exemplary on-site safety feedback mechanisms for a system are disclosed in further detail in U.S. Patent Publication No. 2009/0208365, which is hereby expressly incorporated by reference including, without limitation, the specification, claims, and abstract, as well as any figures, tables, or drawings thereof. Various safety mechanisms can measure pressure, temperature, difference in pressure, difference in temperature, or a combination thereof and provide a perceptible signal if one or more of these increases above a predetermined level. In an aspect, the level of pressure, temperature, difference in pressure, difference in temperature, or a combination thereof at which safety system provides a perceptible signal can be selected to allow intervention to avoid undesirable or unsafe conditions. In a further aspect of the invention, the system is designed to accommodate at least 5 times the pressure of the system (i.e. design pressure), more preferably at least 3 times the pressure of the system, and more preferably at least 1.5-2 times the pressure of the system. In a further aspect, the system is designed for explosion safety ratings, such as for example, according to the American Petroleum Institute (API). In a further aspect of the invention, the system may include pressure relief valves and/or rupture discs.

Methods Employing Performic Acid Compositions

In some aspects, the present disclosure includes methods of using the performic acid forming compositions disclosed herein. In some aspects, the methods of using the compositions employ a chemistry having a pH of from about 0 to about 5 for various antimicrobial and/or bleaching applications. In other aspects, the methods of using the compositions employ a chemistry having a pH of from about 5 to about 9 for various antimicrobial and/or bleaching applications. In still further aspects, the methods of using the compositions employ a chemistry having a pH of from about 5 to about 14 for various bleaching applications.

In some aspects, the present disclosure includes methods of using the performic acid forming compositions and/or performic acids disclosed herein. Performic acid compositions generated according to the embodiments of the invention may be used for a variety of user-identified biocidal and/or anti-microbial purposes. In some aspects, the on-site generated performic acid compositions may be employed for antimicrobial and/or bleaching methods of use. In further aspects, the on-site generated performic acid compositions may be employed for any sanitizing methods of use. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a performic acid composition of the invention. Contacting can include any of numerous methods for applying a composition, such as spraying the composition, immersing the object in the composition, foam or gel treating the object with the composition, wiping the composition or a combination thereof.

In some aspects, a composition obtained according to the methods and apparatus of the present invention includes an amount of a performic acid composition of the present invention effective for killing one or more of the food-borne pathogenic bacteria associated with a food product, including, but not limited to, *Salmonella typhimurium, Salmonellajaviana, Campylobacterjejuni, Listeria monocytogenes*, and *Escherichia coli* O157:H7, yeast, and mold. In some embodiments, the compositions obtained according to the methods and apparatus of the present invention include an amount of a performic acid composition effective for killing one or more of the pathogenic bacteria associated with a health care surfaces and environments including, but not limited to, *Salmonella typhimurium, Staphylococcus aureus, Salmonella choleraesurus, Pseudomonas aeruginosa, Escherichia coli*, mycobacteria, yeast, and mold. The compositions obtained according to the methods and apparatus of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions obtained according to the methods and apparatus of the present invention, as described above, have activity against a wide variety of human pathogens. The present compositions obtained according to the methods and apparatus of the present invention can kill a wide variety of microorganisms on a food processing surface, on the surface of a food product, in water used for washing or processing of food product, on a health care surface, in a health care environment or the like.

The compositions obtained according to the methods and apparatus of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices, restaurants, clean in place applications, laundry or textile applications and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic.

Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions obtained according to the methods and apparatus of the invention can also be applied to soft surfaces such as food and skin (e.g., a hand). The present compositions can be employed as a foaming or nonfoaming environmental sanitizer or disinfectant.

The performic acid compositions obtained according to the methods and system of the present invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people. The compositions can also be employed as an antimicrobial teat dip.

In some aspects, the compositions obtained according to the methods and apparatus of the present invention can be employed for reducing the population of pathogenic microorganisms, such as pathogens of humans, animals, and the like. As one skilled in the art will ascertain, the reducing of pathogenic microorganism populations is particularly suitable for healthcare and institutional applications of use. The compositions exhibit activity against pathogens including fungi, molds, bacteria, spores, and viruses, for example, *S. aureus, E. coli*, Streptococci, *Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The performic acid compositions obtained according to the methods and apparatus of the present invention can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include, but are not limited to, eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The compositions can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the compositions obtained according to the methods and apparatus of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be treated with an antimicrobial and/or disinfected with the composition of the invention. For example, the compositions can also be used on or in ware wash machines, dishware, bottle washers, bottle chillers, warmers, third sink washers, cutting areas (e.g., water knives, slicers, cutters and saws), egg washers or the like. Particular treatable surfaces include, but are not limited to, packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like. The composition can also be used in treating microbes found in aqueous systems associated with petroleum or LP gas recovery or fermentation processes and pulp and paper processes and the like.

A filter containing performic acid compositions of the present invention can reduce the population of microorganisms in air and liquids. Such a filter can remove water and air-borne pathogens such as *Legionella*.

The compositions obtained according to the methods and apparatus of the present invention can be employed for reducing the population of microbes, fruit flies, or other insect larva on a drain or other surface.

The compositions of the present invention can also be employed by dipping food processing equipment into the use solution, soaking the equipment for a time sufficient to sanitize or de-stain the equipment, and wiping or draining excess solution off the equipment. The compositions of the present invention may be further employed by spraying or wiping food processing surfaces with the use solution, keeping the surfaces wet for a time sufficient to sanitize the surfaces, and removing excess solution by wiping, draining vertically, vacuuming, etc.

The compositions obtained according to the methods and system of the present invention may also be used in a method of sanitizing hard surfaces such as institutional type equipment, utensils, dishes, health care equipment or tools, and other hard surfaces.

The compositions of the present invention can also be used for laundry or textile applications. The compositions can be employed by rinsing laundry or textile surfaces with the use solution, keeping the surfaces wet for a sufficient time to wash, de-stain, sanitize, bleach and/or rinse the surface.

The performic acid compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, rinsing the composition, foam or gel treating the object with the composition, applying with a wipe system or a combination thereof.

A concentrate or use concentration of a performic acid composition obtained according to the methods and apparatus of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The compositions can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered performic acid compositions according to the invention, or solutions containing these compositions.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, juices.

A method of sanitizing substantially fixed in-place process facilities includes the following steps. A composition in accordance with various embodiments of the invention is introduced into the process facilities at a temperature in the range of about 4° C. to 60° C. After introduction of the composition, the solution is held in a container or circulated throughout the system for a time sufficient to sanitize the process facilities (e.g., to kill undesirable microorganisms). After the surfaces have been sanitized by means of the present compositions, the solution is drained. Upon completion of the sanitizing step, the system optionally may be rinsed with other materials such as potable water. The compositions can be circulated through the process facilities for 10 minutes or less.

The present methods can include delivering the present composition via air delivery to the clean-in-place or other surfaces such as those inside pipes and tanks. This method of air delivery can reduce the volume of solution required.

Methods for Contacting a Food Product

In some aspects, the present invention provides methods for contacting a food product with compositions according to the invention employing any method or apparatus suitable for applying such compositions. For example, in some embodiments, the food product is contacted by the compositions with a spray of the compositions, by immersion in the compositions, by foam or gel treating with the compositions. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compositions of the present invention to other objects.

The present methods require a certain minimal contact time of the compositions with food product for occurrence of significant antimicrobial effect. The contact time can vary with concentration of the use compositions, method of applying the use compositions, temperature of the use compositions, amount of soil on the food product, number of microorganisms on the food product, type of antimicrobial agent, or the like. The exposure time can be at least about 5 to about 15 seconds. In some embodiments, the exposure time is about 15 to about 30 seconds. In other embodiments, the exposure time is at least about 30 seconds.

In some embodiments, the method for washing a food product employs a pressure spray including compositions of the present invention. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing microorganisms, perhaps due to better exposure of the solution into the crevasses or small colonies containing the microorganisms. The spray solution, before application, can also be heated to a temperature of about 15 to 20° C., for example, about 20 to 60° C. to increase efficacy. The spray stabilized compositions can be left on the food product for a sufficient amount of time to suitably reduce the population of microorganisms, and then rinsed, drained, or evaporated off the food product. Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed compositions to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compounds of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in the liquid compositions of the present invention can be accomplished by any of a variety of methods known to those of skill in the art. For example, the food product can be placed into a tank or bath containing the compositions. Alternatively, the food product can be transported or processed in a flume of the compositions. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the compositions can be rinsed, drained, or evaporated off the food product.

In other embodiments, a food product can be treated with a foaming version of the compositions of the present invention. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, including, for example, alkyl aryl sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In some embodiments, a food product can be treated with a thickened or gelled version of the compositions of the present invention. In the thickened or gelled state the washing solution remains in contact with the food product surface for longer periods of time, thus increasing the antimicrobial efficacy. The thickened or gelled solution will also adhere to vertical surfaces. The compositions can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The compositions of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The compositions of the present invention can be used to sanitize, disinfect, act as a sporicide for, or sterilize bottles, pumps, lines, tanks and mixing equipment used in the manufacture of such beverages. Further, the compositions of the present invention can be used in aseptic, cold filling operations in which the interior of the food, beverage, or pharmaceutical container is sanitized or sterilized prior to filling. In such operations, a container can be contacted with the compositions, typically using a spray, dipping, or filling device to intimately contact the inside of the container with the compositions, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The compositions of the present invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the compositions of the invention can be used to sanitize the interior of beverage containers prior to filling with the carbonated (or noncarbonated) beverage. Typical carbonated beverages in this application include, but are not limited to, cola beverages, fruit beverages, ginger ale beverages, root beer beverages, iced tea beverages which may be non-carbonated, and other common beverages considered soft drinks. The compositions of the invention can be used to sanitize both the tanks, lines, pumps, and other equipment used for the manufacture and storage of the soft drink material and also used in the bottling or containers for the beverages. In an embodiment, the compositions are useful for killing both bacterial and fungal microorganisms that can be present on the surfaces of the production equipment and beverage containers.

Methods for Industrial Processing

In some aspects, the invention includes methods of using the performic acid forming compositions and/or performic acids to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the performic acid forming compositions and/or performic acids are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Equipment configuration and software were developed for on-site generation of performic acid compositions, including performic acid forming compositions and performic acid for use as biocides. A reactor module meeting the hydraulic requirements of the reaction kinetics was developed to obtain precise and repeatable generation of active performic acid chemistry. In addition, a software algorithm was developed to run one or multiple reactor modules to sequence events appropriately to maximize active yield and safely operate the reactor module.

Example 1

Figure 5:
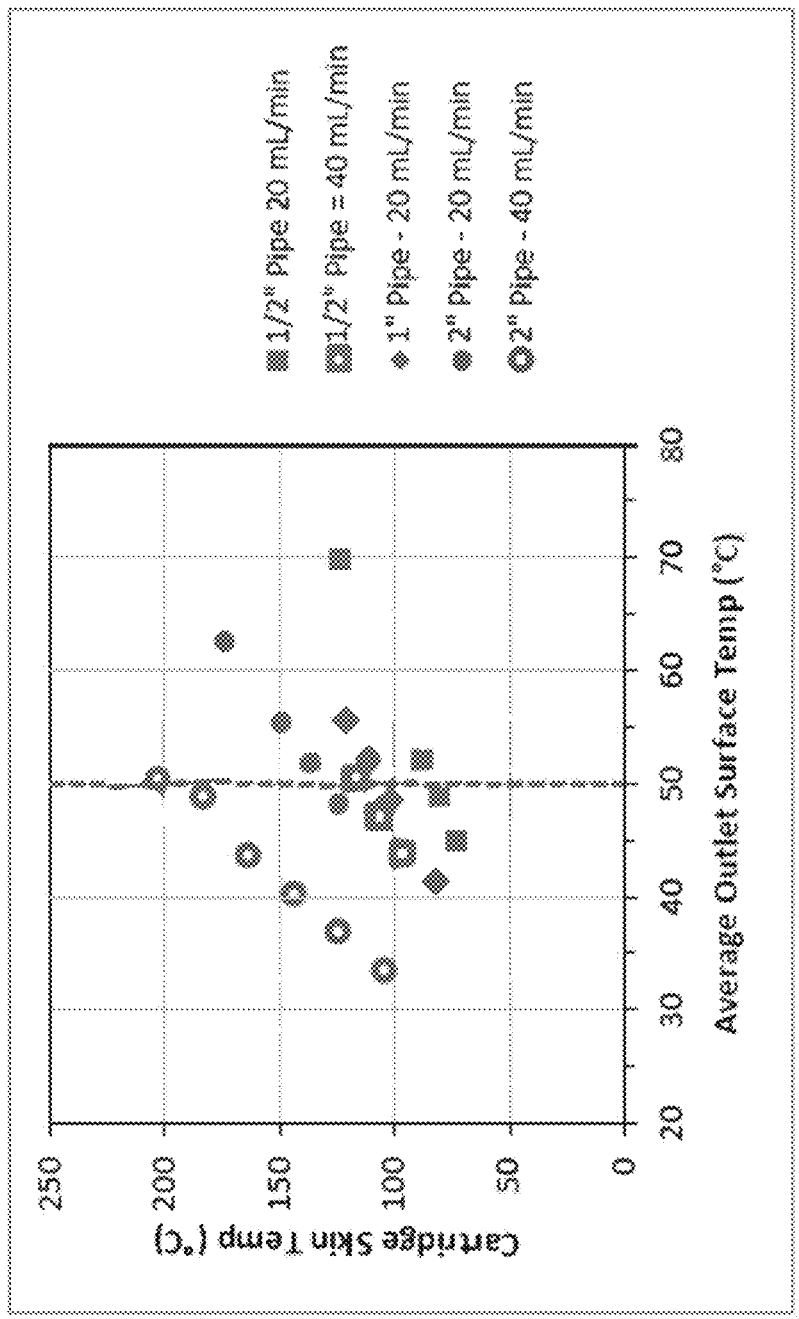
FIG. 5 shows modeling of fluid flow through the reactor according to an embodiment of the invention, indicating a correlation between flow rates, tubing diameter, and temperature of the cartridge
Figure 6:
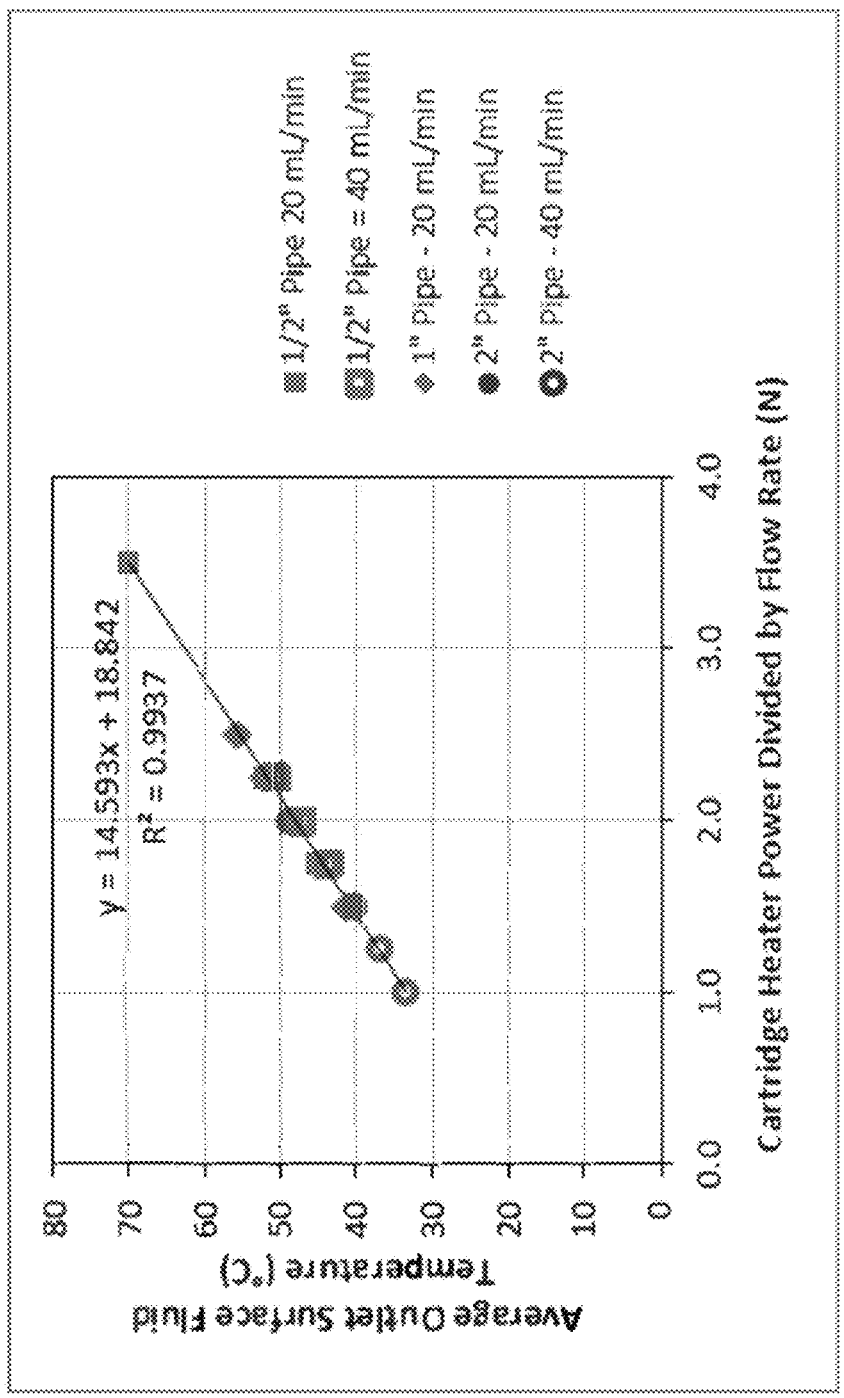
FIG. 6 shows the relationship between fluid bulk temperature cartridge heater skin temperature and flow rate according to an embodiment of the invention.

An exemplary single reaction module was configured according to FIG. 2. In the single reaction module, performic acid were generated through the addition of formic acid and hydrogen peroxide. A number of correlations were developed, for example, FIGS. 5 and 6 illustrate the relationship between fluid bulk temperature, cartridge heater skin temperature, and flow rate. The FIGS. were created using the SolidWorks Computational Fluid Dynamics (CFD) package SolidWorks Flow. A simplified model was set up to analyze the heat transfer characteristics of the Formic acid flow into the generator up to the Hydrogen Peroxide inlet. The model was set up using standard pipe sizes ½", 1", and 2" using stainless steel material properties. A ¼" diameter cartridge heater 6" long was inserted through a tee connector and into a 10" long straight pipe section. Formic acid entered the computational domain at a tee mounted vertically above the cartridge via a 2.5" pipe nipple of the appropriate diameter for each simulation. Using this physical model, two inputs were used to generate the range of data: inlet flow rate and heater power. Formic acid entering the computational domain was set to a flow rate of either 20 or 40 mL/min. The cartridge heater was assumed to generate a uniform surface flux at various power levels to generate the range of data points. For FIG. 5, the cartridge skin temperature reported was the maximum temperature found on any part of the cartridge surface. For both figures, the average outlet surface temperature was taken as an area average of the fluid temperature across a plane normal to the flow at the end of the 10 inch long pipe section.

According to FIG. 5, there is an approximately linear relationship between the average outlet surface temperature and the skin temperature of the cartridge. Additionally, FIG. 6 indicates that the heater power divided by the flow rate is linearly related to the average outlet surface fluid temperature.

Figure 7:
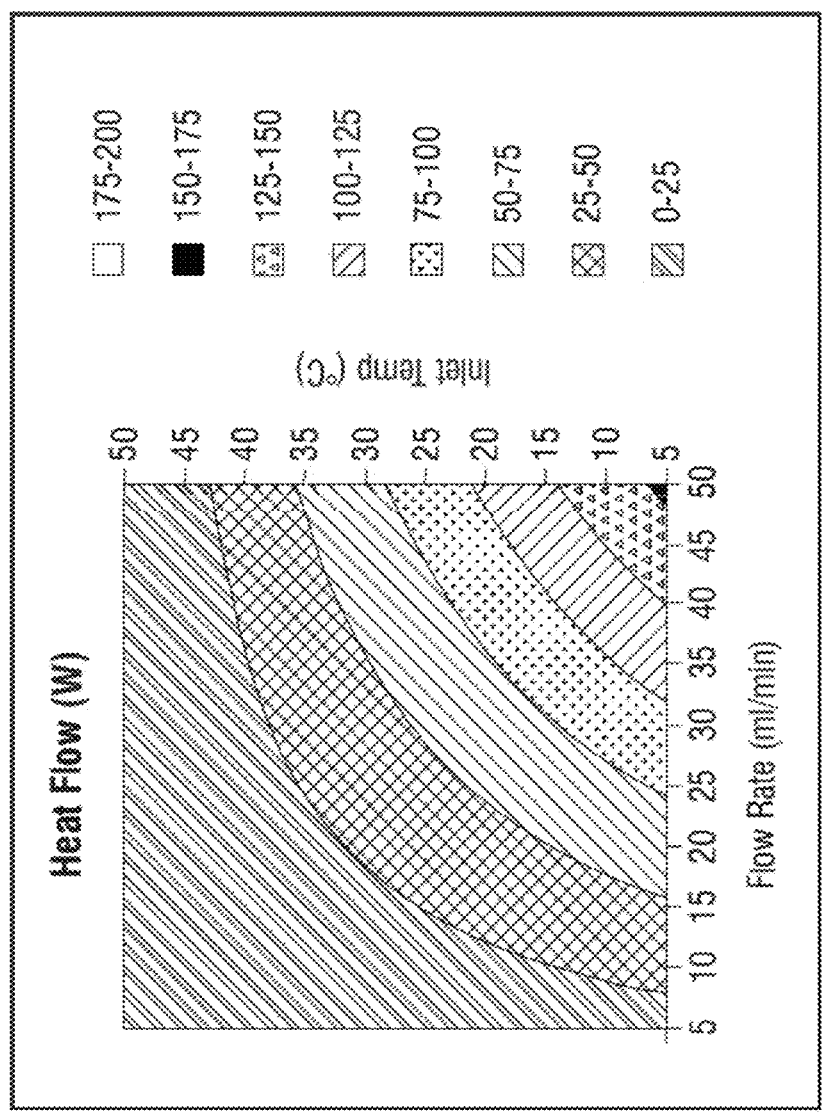
FIG. 7 shows the effect of reagent inlet temperature and heater power according to an embodiment of the invention.

Furthermore, FIG. 7 illustrates Heat Flow on a contour plot of Flow Rate vs. Inlet Temp. The depicted data comes from an equation that sets an outlet temperature of 50° C. at the end of a heating element, and assumes all of the heat coming from the heating element in the performic acid generator is transferred into the fluid flowing past the heating element. This gives a minimum value for the amount of heat required. The figure shows the effect of reagent inlet temperature and heater power, in that the higher heater power is required for higher flow rates and low reagent temperatures may lead to thermal decomposition of the reagent. Such a problem may be resolved by employing staged heaters and/or adjusting the size of the heating element.

Example 2

An exemplary single reaction module is configured according to FIG. 2. The control software maintained a set point temperature of 50° C. at the point of adding the peroxide source to the warm formic acid. A formic acid to peroxide premix formulation of 5.21:1 was used over a series of titrations. An iodometric titration procedure is utilized. Approximately 200 g of deionized ice water is added to an Erlenmeyer flask along with about 0.30 to about 0.50 grams of sample. The final sample size is recorded for later calculations. Approximately 2 mL of glacial acetic acid, 5 mL of 10% potassium iodine solution and 2 mL of starch is added to the sample which is then placed on a stir plate and immediately titrated with 0.1 N sodium thiosulfate titrant to a colorless endpoint that persisted for at least 20 seconds. Volume of the titrant used is recorded as titrant 1 for later calculations. To the same flask, approximately 3 mL of 9 N sulfuric acid and 2 mL ammonium molybdate, which is then allowed to rest in the sample for approximately 2 to 3 minutes. The flask is then placed on a stir plate and immediately titrated with 0.1 N sodium thiosulfate titrant to a second colorless endpoint that persists for at least 20 seconds. Volume of the titrant used is recorded as titrant 2 for later calculations. Table 1 indicates the results of the iodometric titration method and subsequent calculations for measuring the performic acid and hydrogen peroxide.

TABLE 1

Titration Data

| % Performic Acid | % Hydrogen Peroxide |
| --- | --- |
| 5.48 | 0 |
| 5.30 | 0 |
| 5.57 | 0.21 |

Table 1 shows the ratio of performic acid to hydrogen peroxide generated according to the in situ synthesis of performic acid in the apparatus of the invention.

Example 3

An exemplary single reaction module is configured according to FIG. 2. A conductivity probe was used to take measurements of the reaction. Use of a conductivity probe provides an electroanalytical method to measure various parameters of a product. An exemplary conductivity sensors comprises two electrodes, and operates by applying a voltage across the two electrodes and measuring a resulting current. The relationship between the magnitudes of the current and the voltage allow the resistance and therefore conductivity of the product to be determined.

Figure 8:
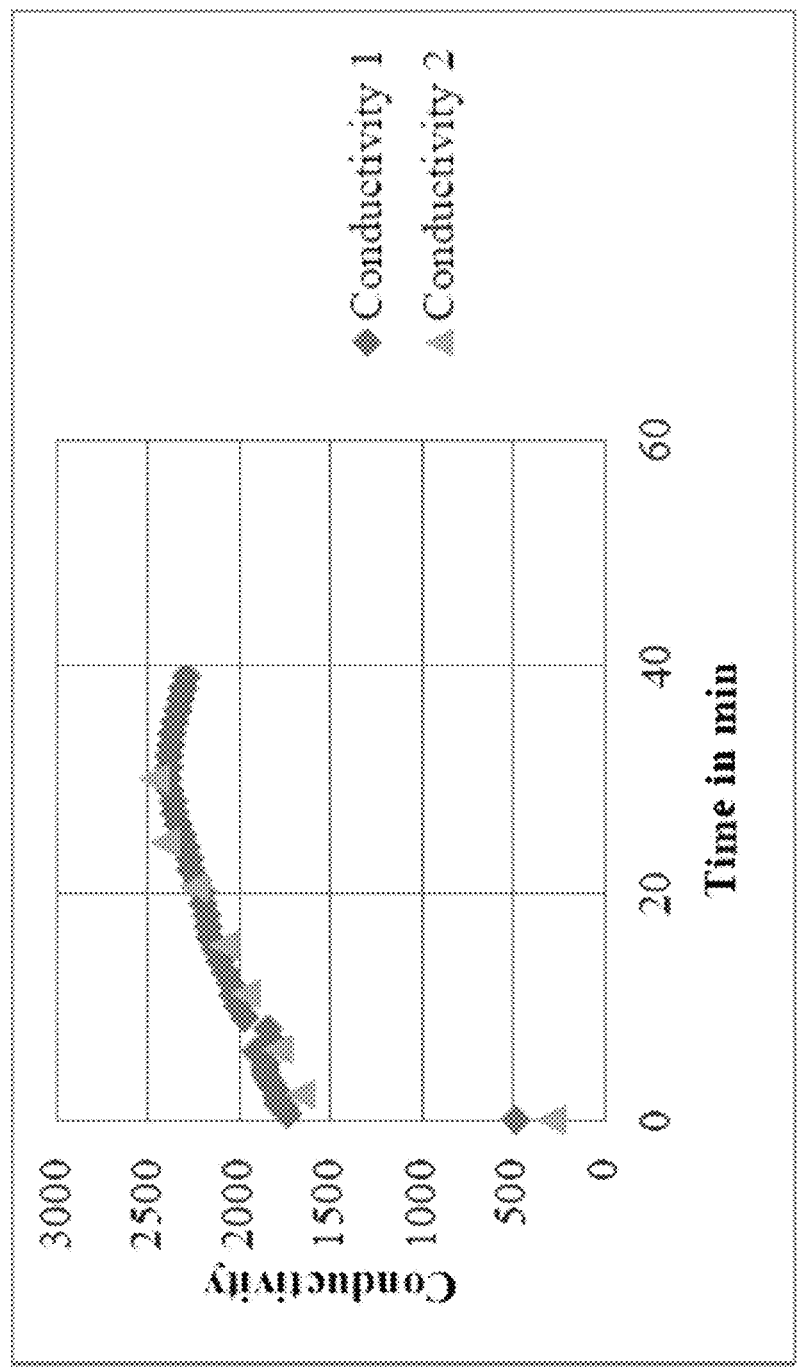
FIG. 8 shows conductivity measured from two independent experiments designed to generate performic acid by mixing of formic acid and hydrogen peroxide according to an embodiment of the invention.

FIG. 8 illustrates the results of the experiments. Conductivity of a solution of reactants and products is higher than a solution of reactants alone. Table 2 further illustrates the correlation between conductivity and performic acid concentration.

TABLE 2

Conductivity Data

| % Performic Acid | Conductivity ($\mu$S/cm) |
| --- | --- |
| 0 | 358 |
| 0.9 | 2120 |
| 4.49 | 2421 |
| 5.02 | 2631 |
| 7.44 | 2675 |
| 8.525 | 2920 |

Example 4

The system according to an embodiment of the invention was assembled, including a downward flow of the oxidizing agent inlet. The system was operated with a 97% formic acid concentration inlet flow of 17.6 mL/min and a 35% hydrogen peroxide concentration inlet flow of 2.4 mL/min. Samples were collected at 2, 5, 10, and 15 minutes and tested according to the iodometric titration procedure according to Example 2 for performic acid concentration and hydrogen peroxide concentration. These results are shown in Table 3 and FIG. 11.

TABLE 3

Titration Data

| Elapsed Time (min) | % Performic Acid | % Hydrogen Peroxide |
| --- | --- | --- |
| 2 | 8.28 | 1.75 |
| 5 | 8.84 | 1.06 |
| 10 | 7.30 | 0.33 |
| 15 | 9.02 | 0.50 |

Figure 11:
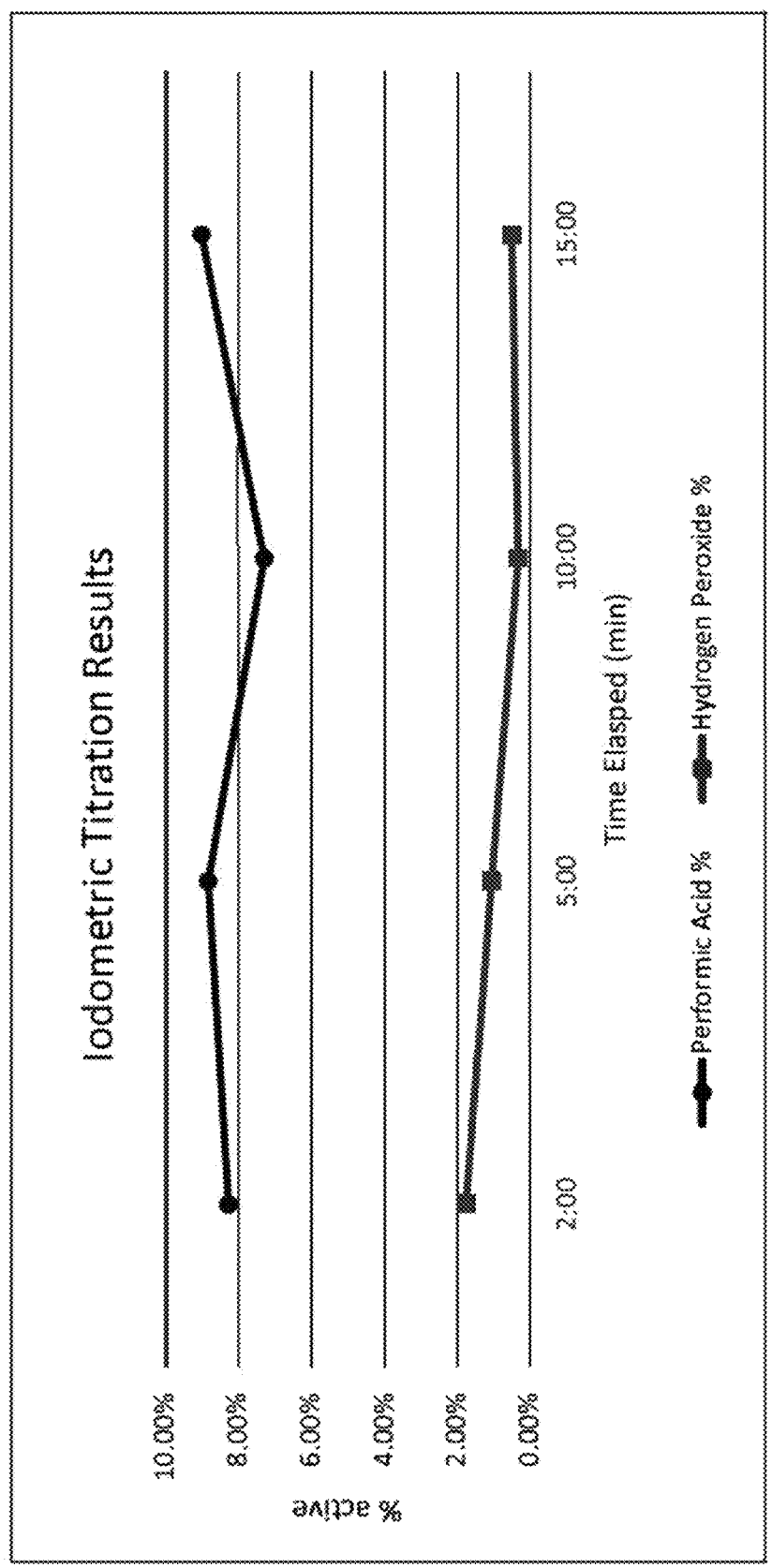
FIG. 11 shows experimental results demonstrating iodometric titration of performic acid generated by an adjustable biocide formulator apparatus according to an embodiment of the invention.

The results shown in Table 3 and FIG. 11 indicate that the performic acid concentration had reached a stable concentration with a standard deviation of 0.007 within the first 2 minutes of the reaction.

Example 5

The peroxyformic acid generator according to the embodiments depicted in the figures having multiple inlets to provide formic acid blend (formic acid, catalyst and corrosion inhibitor) as well as hydrogen peroxide was evaluated under field conditions at a scale-up volume. The generator was used at a salt water disposal well.

Beneficially, the PFA generated exceeded expectations in lab analysis. Approximately 15% of PFA was generated at the site of dosing. The sampling points were both at the top and bottom sampling ports from laboratory generation compared to in the field generation are shown in Table 4.

TABLE 4

PFA Generation

| Formic acid blend | 35% peroxide | % PFA | % Hydrogen Peroxide | Location | Residence Time (feet) | Temperature (F.) |
|---|---|---|---|---|---|---|
| 90 | 10 | 8.2 | 0.17 | Lab | 10 | 120 |
| 81 | 19 | 9.61 | 0.85 | Lab | 10 | 120 |
| 70 | 30 | 11.94 | 2.72 | Lab | 10 | 120 |
| 67 | 33 | 11.78 | 2.98 | Lab | 10 | 120 |
| 75 | 25 | 15.5 | 1.4 | Field | 90 | 100-105 |
| 80 | 20 | 12.92 | 0.85 | Field | 90 | 100-105 |
| 88 | 12 | 7.1 | 0.2 | Field | 90 | 100-105 |
| 85 | 15 | 10.85 | 0 | Field | 90 | 100-105 |

The increase in PFA generation is attributed to the modification of the high ambient temperatures coupled with the long residual time of the formic/peroxide mixture provided by the tubing from the point of generation to the site of dosing (90 ft). Peroxide flow and formic acid flow were monitored via flow meters. Product formation was monitored via conductivity as well as titration methods. Temperatures were monitored using probes in the generator. Flow of peroxide was challenged due to excessive heat as well as the pumps ceasing because of air, which are subject to modification through auto-priming valves as well as vent valves that will remove air from the tubing allowing for bubble free flow.

Example 6

Figure 13:
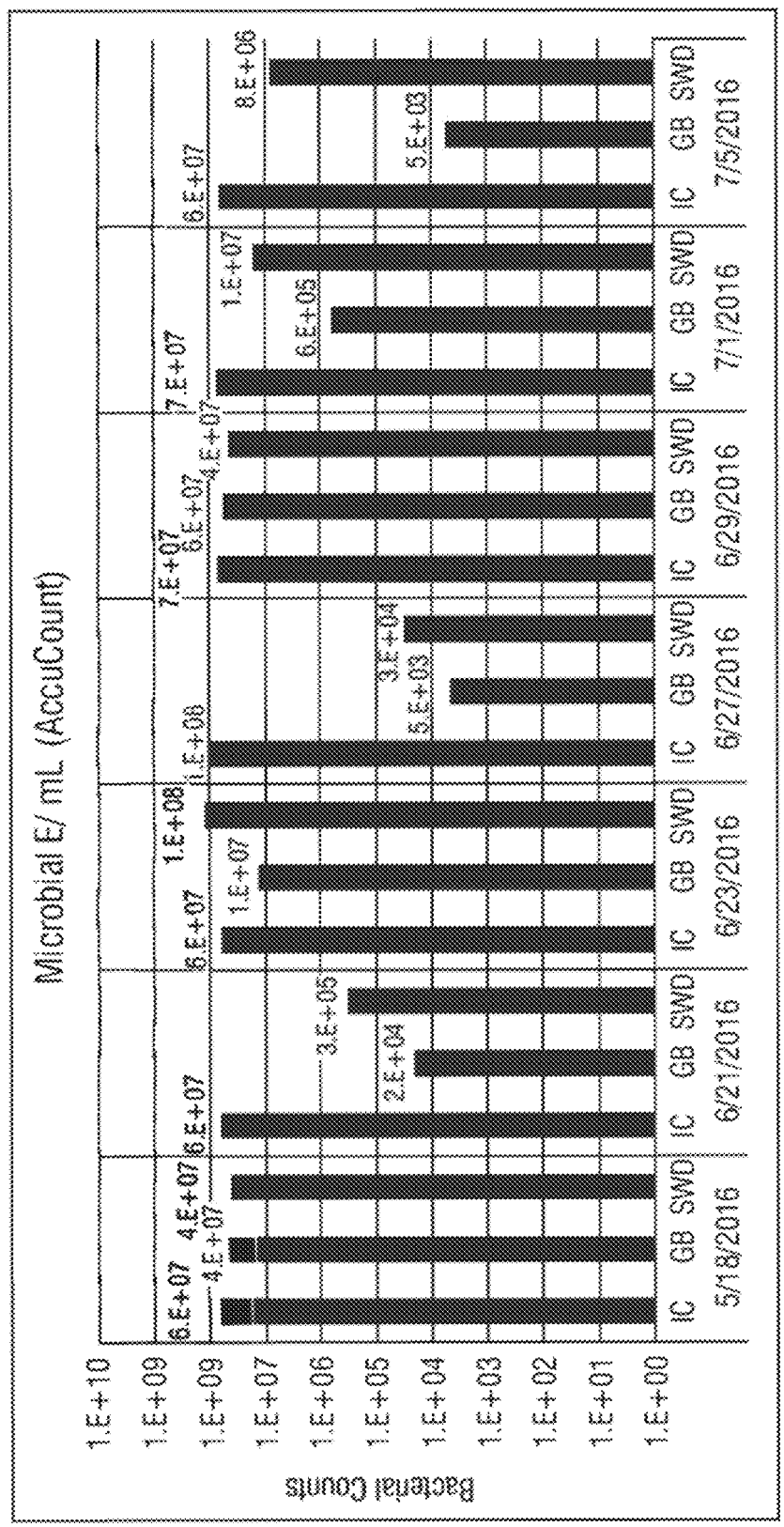
FIG. 13 shows experimental results demonstrating microbial efficacy of PFA generated according to an exemplary embodiment of the invention.

The performance of the chemistry generated in the field according to Example 5 was evaluated for micro efficacy. PFA dosed at 250 ppm (~25 ppm active) indicates at least reduction in microbial numbers equivalent to 2-3 logs, as shown in FIG. 13. In the figures the GB refers to site of treatment (gun barrel) measurement, whereas SWD refers to the disposal water measurement for micro efficacy.

The percentage reduction of microbial numbers compared to incoming water was also evaluated. Microbial numbers were monitored using traditional serial dilution bug bottles that select for SRB or APB populations. All results showed at least a 2-3 log reduction and in some case a 7 log reduction in microbial population.

Figure 14:
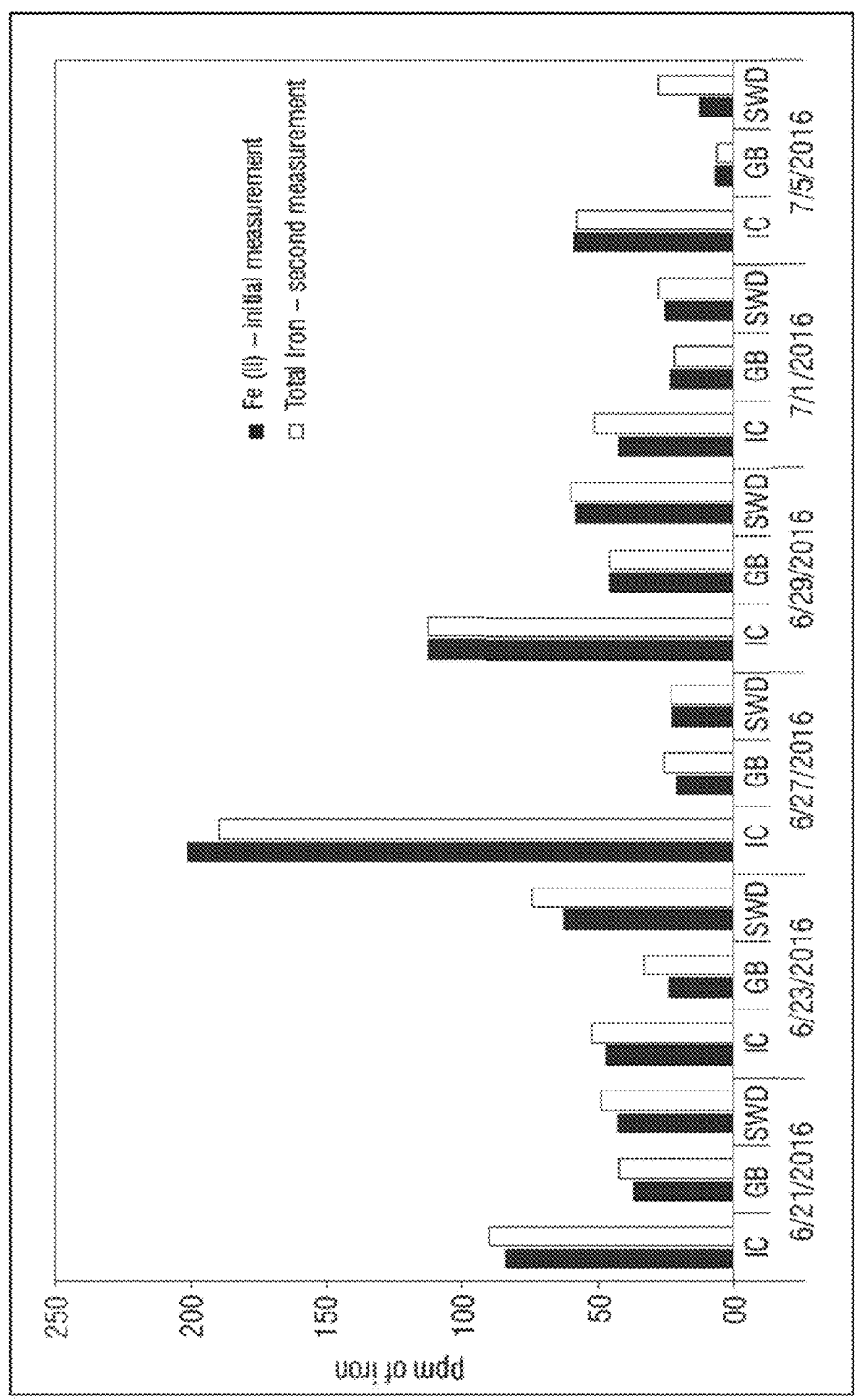
FIG. 14 shows experimental results demonstrating PFA oxidizing FeS into iron oxide according to an exemplary embodiment of the invention.

The iron oxidation potential of PFA was further evaluated as PFA is an oxidant and is capable of oxidizing FeS into iron oxide. Samples drawn from the incoming water, site of treatment (gun barrel) and disposal water (SWD) indicates a reduction in FeS concentration during treatment, as shown in FIG. 14. A consequence of this is an increased oil production. Beneficially, disposal waters tested at the initial of PFA treatment and after 15 days of treatment and a reduction of FeS was observed. FeS can be oil wet and holds a lot of oil. Upon oxidation this oil is released. BS&W analysis provides a quantitative estimation on the amount of water, solids, emulsion and oil present in the samples. This analysis on the two samples indicates 97% oil which is 92% increase in the total recoverable oil before and after treatment with PFA.

The inventions being thus described, it will be obvious that the same may be varied in many ways. Such variations are not to be regarded as a departure from the spirit and scope of the inventions and all such modifications are intended to be included within the scope of the following claims.

What is claimed:

1. An adjustable biocide generator system for on-site performic acid forming composition generation comprising:
    an apparatus comprising at least one inlet, a length of pipe, a heating device, an outlet, and a storage reservoir for dosing a performic acid forming composition from said length of pipe;
    wherein said inlet(s) are in fluid connection with said length of pipe and supply reagents to produce said performic acid forming composition in said length of pipe;
    wherein said reagents comprise a formic acid source and an oxidizing agent; and
    wherein said length of pipe is in fluid connection with said outlet to dispense said performic acid forming composition to a storage reservoir.

2. The system according to claim 1, wherein said performic acid forming composition is an individual or mixed performic acid forming composition according to a user- or system-inputted selection, and wherein the mixed performic acid forming composition comprises performic acid and an additional C1-C22 percarboxylic acid.

3. The system according to claim 1, wherein the formic acid source is formic acid, and wherein said oxidizing agent is 1-50% w/v hydrogen peroxide.

4. The system according to claim 1, wherein the length of pipe further comprises a cooling system prior to dispensing said performic acid forming composition to the storage reservoir.

5. The system according to claim 4, wherein the cooling system includes a quenching mode, increased surface area, cooling jacket, venting systems, cold finger, heat exchanger, refrigeration sleeve, blower, cooled vessel, or combinations thereof.

6. The system according to claim 1, further comprising at least one measurement device, wherein said measurement device measures one or more reaction kinetics or system operations for said performic acid forming composition generation.

7. The system according to claim 1, wherein said heating device is selected from the group consisting of a cartridge, heat exchanger, heat blanket, steam jacket, solar panels, steam preheat, an electrical source and combinations thereof, and wherein said heating device maintains a temperature that does not exceed 200° C. for the reagent temperature, and wherein said length of pipe is designed to accommodate at least 5 times the pressure of the system.

8. The system according to claim 1, further comprising a control software for operating said apparatus to generate a user- or system-inputted performic acid forming composition and desired flow rate of said performic acid forming composition for on-site generation, wherein said control software determines the flow rate and/or timing of feeding of said raw materials to said length of pipe and reaction time required for production of said user- or system-inputted performic acid forming composition and desired flow rate.

9. The system according to claim 1, wherein the storage reservoir comprises a cooling system to cool the performic acid forming composition.

10. The system according to claim 9, wherein the cooling system includes a cooling jacket, venting systems, cold finger, heat exchanger, refrigeration sleeve, blower, cooled vessel or combinations thereof.

11. A method of on-site generating performic acid forming composition comprising:
providing a formic acid source to a length of pipe at a desired flow rate;
providing an oxidizing agent to said length of pipe at a desired flow rate;
contacting said formic acid source with an effective amount of said oxidizing agent within said length of pipe in the presence of a heating device to form a performic acid composition;
delivering said performic acid composition to a downstream storage reservoir, wherein said performic acid is an individual or mixed performic acid composition according to a user- or system-inputted selection,
wherein the reaction to form the performic acid composition begins generating yield instantaneously and reaches maximum yield within 10 minutes or less.

12. The method of claim 11, wherein the formic acid source is formic acid and the oxidizing agent is hydrogen peroxide, and wherein the hydrogen peroxide and the performic acid concentration generated on-site is from 2 wt-% to about 15 wt-% and has a higher concentration to the unreacted hydrogen peroxide.

13. The method of claim 11, wherein said storage reservoir comprises a cooling system to cool the performic acid composition.

14. The method of claim 13, wherein the cooling system includes a cooling jacket, venting systems, cold finger, heat exchanger, refrigeration sleeve, blower, cooled vessel or combinations thereof.

15. The method of claim 11, further comprising a cooling system for cooling said performic acid prior to the storage reservoir.

16. The method of claim 15, wherein the cooling system includes a quenching mode, increased surface area, cooling jacket, venting systems, cold finger, heat exchanger, refrigeration sleeve, blower, cooled vessel or combinations thereof.

17. The method of claim 11, further comprising a step of: (a) measuring variables of the reaction to form the performic acid composition, wherein the measuring step measures conductivity, temperature, product levels, concentrations, IR/UV/VIS spectroscopy, pressure, performic acid and/or oxidant concentrations, and/or flow rate; and/or (b) controlling the method using control software for operating said apparatus to generate a user- or system-inputted performic acid forming composition and said desired flow rate of said performic acid forming composition for on-site generation.

18. The method according to claim 11, wherein the reaction reaches maximum yield within 60 seconds or less, wherein the reaction generates at least about 2% performic acid near instantaneously, the reaction generates at least about 4% performic acid within 1 minute, the reaction generates at least about 8% performic acid within 2 minutes, or the reaction generates at least 15% performic acid within 30 minutes.

19. A method of cleaning using an on-site generated performic acid composition comprising:
obtaining a user- or system-inputted performic acid composition on-site using an adjustable biocide generator system comprising:
an apparatus comprising at least one inlet, a length of pipe, a heating device, an outlet, and a storage reservoir for dosing a performic acid forming composition from said length of pipe;
wherein said inlet(s) are in fluid connection with said length of pipe and supply reagents to produce said performic acid forming composition in said length of pipe;
wherein said reagents comprise a formic acid source and an oxidizing agent and wherein said length of pipe is in fluid connection with said outlet to dispense said performic acid forming composition to a storage reservoir;
applying said performic acid composition in an amount sufficient to sanitize, bleach and/or disinfect a surface in need thereof.

20. The method of claim 19, wherein the surface is a food item or a plant item and/or at least a portion of a medium, a container, an equipment, a membrane, a system or a facility for growing, holding, processing, packaging, storing, transporting, preparing, cooking or serving the food item or the plant item, and wherein the performic acid composition is applied to the surface by means of a spray, immersion, foam, or gel.

* * * * *

UNITED STATES PATENT AND TRADEMARK OFFICE
CERTIFICATE OF CORRECTION

PATENT NO. : 11,737,460 B2
APPLICATION NO. : 16/946513
DATED : August 29, 2023
INVENTOR(S) : Paul R. Kraus et al.

Page 1 of 1

It is certified that error appears in the above-identified patent and that said Letters Patent is hereby corrected as shown below:

In the Claims

Column 46, Claim 19, Lines 35-37:
DELETE: "agent" after "oxidizing"
INSERT: --agent;-- after "oxidizing"

Column 46, Claim 19, Lines 35-37:
DELETE: "wherein said length of pipe is in fluid connection with said outlet to dispense said performic acid forming composition to a storage reservoir;"
INSERT AS NEW LINE 36: --wherein said length of pipe is in fluid connection with said outlet to dispense said performic acid forming composition to a storage reservoir;--

Signed and Sealed this
Second Day of January, 2024

Katherine Kelly Vidal
*Director of the United States Patent and Trademark Office*